United States Patent
Kitahashi et al.

(10) Patent No.: US 11,182,893 B2
(45) Date of Patent: Nov. 23, 2021

(54) METHOD OF PRETREATING SAMPLE INCLUDING BIOLOGICAL PARTICLES, METHOD OF ACQUIRING IMAGE OF BIOLOGICAL PARTICLES, APPARATUS FOR PRETREATING SAMPLE INCLUDING BIOLOGICAL PARTICLES, AND BIOLOGICAL PARTICLE IMAGE-ACQUIRING APPARATUS

(71) Applicant: Japan Agency for Marine-Earth Science and Technology, Yokosuka (JP)

(72) Inventors: Tomo Kitahashi, Yokosuka (JP); Hiromi Watanabe, Yokosuka (JP); Masashi Tsuchiya, Yokosuka (JP); Hiroyuki Yamamoto, Yokosuka (JP)

(73) Assignee: Japan Agency for Marine-Earth Science and Technology, Yokosuka (JP)

( * ) Notice: Subject to any disclaimer, the term of this patent is extended or adjusted under 35 U.S.C. 154(b) by 317 days.

(21) Appl. No.: 16/321,325

(22) PCT Filed: Nov. 27, 2017

(86) PCT No.: PCT/JP2017/042355
§ 371 (c)(1),
(2) Date: Jan. 28, 2019

(87) PCT Pub. No.: WO2018/101194
PCT Pub. Date: Jun. 7, 2018

(65) Prior Publication Data
US 2019/0172204 A1    Jun. 6, 2019

(30) Foreign Application Priority Data

Nov. 30, 2016 (JP) ............... JP2016-232868

(51) Int. Cl.
*G01N 15/00* (2006.01)
*G01N 15/14* (2006.01)
(Continued)

(52) U.S. Cl.
CPC ............. *G06T 7/0012* (2013.01); *C12M 1/00* (2013.01); *C12N 1/02* (2013.01); *G01N 1/10* (2013.01);
(Continued)

(58) Field of Classification Search
CPC ... B82Y 5/00; C12M 1/00; C12N 1/02; G01N 15/00; G01N 15/1459; G01N 15/1463;
(Continued)

(56) References Cited

U.S. PATENT DOCUMENTS

2014/0146157 A1    5/2014  Duplisea et al.
2015/0232911 A1*   8/2015  Rowlen ................. C12Q 1/24
                                                    435/5
2017/0095772 A1*   4/2017  Kim ..................... B01D 69/02

FOREIGN PATENT DOCUMENTS

CN    1762612 A      4/2006
CN    202943033 U    5/2013
(Continued)

OTHER PUBLICATIONS

International Search Report and Written Opinion dated Feb. 13, 2018 in connection with PCT/JP2017/042355.
(Continued)

*Primary Examiner* — Maureen Wallenhorst
(74) *Attorney, Agent, or Firm* — Wolf, Greenfield & Sacks, P.C.

(57) ABSTRACT

A method of pretreating a sample including biological particles, the method including a step of acquiring a fraction (1b) which passes through a sieve (A) having meshes of 250 to 1000 μm and does not pass through a sieve (B) having
(Continued)

meshes of 32 to 63 μm by sieving a sample including biological particles as a detection target, and a step of adding a colloidal solution having a density of 1.10 to 2.45 g/cm$^3$ to the fraction (1b), subjecting the resultant solution to centrifugation, and acquiring a supernatant fraction (S0) after the centrifugation.

8 Claims, 6 Drawing Sheets

(51) Int. Cl.
  *G01N 1/10* (2006.01)
  *G01N 21/64* (2006.01)
  *G06T 7/00* (2017.01)
  *C12M 1/00* (2006.01)
  *C12N 1/02* (2006.01)
  *B82Y 5/00* (2011.01)

(52) U.S. Cl.
  CPC ......... *G01N 15/00* (2013.01); *G01N 21/6458* (2013.01); *B82Y 5/00* (2013.01); *G01N 15/1459* (2013.01); *G01N 15/1463* (2013.01); *Y10T 436/255* (2015.01); *Y10T 436/25375* (2015.01)

(58) Field of Classification Search
  CPC ............. G01N 1/10; G01N 2015/1006; G01N 21/6458; G06T 7/0012; Y10T 436/25; Y10T 436/25125; Y10T 436/25375; Y10T 436/255
  USPC ..... 436/164, 174, 175, 177, 178; 422/82.05, 422/527, 533, 534, 535
  See application file for complete search history.

(56) References Cited

FOREIGN PATENT DOCUMENTS

| | | |
|---|---|---|
| CN | 105283742 A | 1/2016 |
| CN | 105454027 A | 4/2016 |
| CN | 106048047 A | 10/2016 |
| EP | 17875370.3 | 1/2020 |
| KR | 20090062482 A | 6/2009 |
| KR | 20160064490 A | 6/2016 |
| WO | 2010/096107 A1 | 8/2010 |

OTHER PUBLICATIONS

Burgess, An improved protocol for separating meiofauna from sediments using colloidal silica sols, Marine Ecology Progress Series. 2001;214:161-5.
Carstensen et al., 7. 08—Coastal Monitoring Programs, Treatise on Estuarine and Coastal Science. 2011;7:175-206.
Grego et al., Main meiofauna taxa as an indicator for assessing the spatial and seasonal impact of fish farming. Mar Pollut Bull. Aug. 2009;58(8):1178-1186. doi: 10.1016/j.marpolbul.2009.03.020. Epub Apr. 23, 2009.
Extended European Search Report dated Jan. 31, 2020 in connection with European Patent Application No. EP17875370.3.
Mevenkamp et al., Experimental evidence for selective settlement of meiofauna from two distinct environments after sediment suspension. Journal of Experimental Marine Biology and Ecology. Nov. 3, 2016;474:195-203. doi: 10.1016/J.JEMBE.2015.10.005.
[No Author Listed] Ludox-Technical literature. 2016;1-4.
Lin et al., Studies on the meiofauna community in paddy field of the midlle of Shandong. J Jinggangshan University Natural Science. 2010;31(4):110-112.
Wang et al., Abundance and biomass of meiobenthos in the Beibu Gulf. Ecological Science. 2011;30:375.
Wang et al., An Improved Study on Ludox Centrifugal Separation Method of Deep-sea Small Benthic Organisms. J Marine Science, 2010;28(3):79-84.
Chinese Office Action for Application No. 201780047061.5 dated Jul. 20, 2021.

\* cited by examiner

METHOD OF PRETREATING SAMPLE INCLUDING BIOLOGICAL PARTICLES, METHOD OF ACQUIRING IMAGE OF BIOLOGICAL PARTICLES, APPARATUS FOR PRETREATING SAMPLE INCLUDING BIOLOGICAL PARTICLES, AND BIOLOGICAL PARTICLE IMAGE-ACQUIRING APPARATUS

CROSS-REFERENCE TO RELATED APPLICATIONS

This Application is a National Stage filing under 35 U.S.C. 371 of International Patent Application Serial No. PCT/JP2017/042355, filed Nov. 27, 2017, which claims foreign priority benefits under 35 U.S.C. § 119(a)-(d) or 35 U.S.C. § 365(b) of Japanese Application Number 2016-232868, filed Nov. 30, 2016. The entire contents of these applications are incorporated herein by reference in their entirety.

TECHNICAL FIELD

The present invention relates to a method of pretreating a sample including biological particles, a method of acquiring an image of biological particles, an apparatus for pretreating a sample including biological particles, and a biological particle image-acquiring apparatus.

BACKGROUND ART

Meiofauna is a generic name for organisms which pass through a sieve having meshes of 1 mm and are captured by a sieve having meshes of 32 Meiofauna are known to greatly affect material circulation and sediment stability and are an important component of the deep ocean ecosystem. In addition, the generation time is short and meiofauna respond quickly to environmental changes; therefore, it is easy to detect environmental changes with using meiofauna. Furthermore, meiofauna are easy to be statistically analyzed since the population density is high, even on the deep-sea floor where the population density of organisms is low, and quantitative collection thereof is also easy. From these facts, meiofauna are regarded as important target organisms for environmental impact assessments on the deep-sea floor.

In the related art, the discrimination and counting of types of meiofauna, which are performed by microscopic observation, require fine operations. Therefore, processing one sample takes a huge amount of time. In a case of carrying out an environmental impact assessment, it is necessary to process a large number of samples, thus, processing all the samples may take several years or longer. In addition, expert knowledge and dexterity are necessary for analysis by microscopic observation and it is also difficult to reliably secure such personnel. Furthermore, in analysis by microscopic observation, it is possible for variations in the analysis results to occur among the observers.

On the other hand, as an apparatus for analyzing particles in a fluid, for example, the apparatus described in PTL 1 was proposed. The apparatus described in PTL 1 is provided with a fluid dilution system and a particle imaging system and, in a case where a sample fluid is opaque or viscous, the fluid dilution system performs dilution of the sample fluid. The fluid dilution system is controlled to operate in a case where an image acquired with the particle imaging system is blurred.

CITATION LIST

Patent Literature

[PTL 1] United States Patent Application, Publication No. 2014/0146157

SUMMARY OF INVENTION

Technical Problem

In the apparatus described in PTL 1, the fluid dilution system operates in a case where the image acquired with the particle imaging system is blurred, thus, the sample fluid before the fluid dilution system operates is wasted. In addition, in a case of targeting organisms living in sediment such as meiofauna, the number of sediment particles with respect to the target biological particles is overwhelmingly large in samples collected from the seafloor or the like. Therefore, it is difficult to observe the target biological particles only using dilution. Furthermore, when a sample including a large amount of sediment particles is poured into a flow cell to be used by a particle imaging system, there is also a problem in that the sediment particles clog the flow cell and flow line. On the other hand, when an attempt is made to dilute the sample to such a degree that the flow cell is not clogged with the sediment particles, the amount of the sample introduced into the flow cell becomes enormous, which is not practical.

It is therefore an object of the present invention to provide a technique capable of quickly analyzing biological particles even in a case where sediment particles are present.

Solution to Problem

One aspect of the present invention is a method of pretreating a sample including biological particles, the method including a step of acquiring a fraction (1b) which passes through a sieve (A) having meshes of 250 to 1000 μm and does not pass through a sieve (B) having meshes of 32 to 63 μm by sieving a sample including biological particles as a detection target, and a step of adding a colloidal solution having a density of 1.10 to 2.45 g/cm$^3$ to the fraction (1b), subjecting the resultant solution to centrifugation, and acquiring a supernatant fraction (S0) after the centrifugation.

One aspect of the present invention is a method of pretreating a sample including biological particles, the method including a step of acquiring a fraction (1b) which passes through a sieve (A) having meshes of 250 to 1000 μm and does not pass through a sieve (B) having meshes of 32 to 63 μm by sieving a sample including biological particles as a detection target, a step of adding a colloidal solution having a density of 1.10 to 2.45 g/cm$^3$ to the fraction (1b), subjecting the resultant solution to centrifugation, and acquiring a supernatant fraction (S0) after the centrifugation, a step of suspending a precipitate after the centrifugation in a colloidal solution to perform centrifugation and acquiring a supernatant fraction (Sn) after the centrifugation, n times (n is an integer of 1 or more, the precipitate (Pn−1) is a precipitate obtained after the (n−1)$^{th}$ centrifugation, and the supernatant fraction (Sn) is the supernatant fraction obtained after the n$^{th}$ centrifugation).

One aspect of the present invention is the method of pretreating a sample including biological particles, further including a step of sieving the supernatant fraction (S0) with a sieve (C) having meshes smaller than meshes of the sieve (B) to acquire a fraction which does not pass through the sieve (C), and adding a colloidal solution to the fraction.

One aspect of the present invention is the method of pretreating a sample including biological particles, further including a step of sieving the supernatant fractions (S1) to (Sn) with a sieve (C) having meshes smaller than meshes of the sieve (B) to acquire a fraction which does not pass through the sieve (C), and adding a colloidal solution to the fraction.

One aspect of the present invention is the method of pretreating a sample including biological particles, in which the biological particles are meiofauna.

One aspect of the present invention is the method of pretreating a sample including biological particles, in which the colloidal solution is colloidal silica.

One aspect of the present invention is the method of pretreating a sample including biological particles, in which the biological particles have been stained with a dye.

One aspect of the present invention is a method of acquiring an image of biological particles, the method including a step of acquiring a fraction (1b) which passes through a sieve (A) having meshes of 250 to 1000 µm and does not pass through a sieve (B) having meshes of 32 to 63 µm by sieving a sample including biological particles as a detection target, a step of adding a colloidal solution having a density of 1.10 to 2.45 g/cm$^3$ to the fraction (1b), subjecting the resultant solution to centrifugation, and acquiring a supernatant fraction (S0) after the centrifugation, and a step of allowing a fluid including at least a part of the supernatant fraction (S0) to flow in the flow cell and imaging the fluid flowing in the flow cell.

One aspect of the present invention is a method of acquiring an image of biological particles, the method including a step of acquiring a fraction (1b) which passes through a sieve (A) having meshes of 250 to 1000 µm and does not pass through a sieve (B) having meshes of 32 to 63 µm by sieving a sample including biological particles as a detection target, a step of adding a colloidal solution having a density of 1.10 to 2.45 g/cm$^3$ to the fraction (1b), subjecting the resultant solution to centrifugation, and acquiring a supernatant fraction (S0) after the centrifugation, a step of suspending a precipitate (Pn−1) after the centrifugation in the colloidal solution to perform centrifugation and acquiring a supernatant fraction (Sn) after the centrifugation, n times (n is an integer of 1 or more, the precipitate (Pn−1) is a precipitate obtained after the (n−1)$^{th}$ centrifugation, and the supernatant fraction (Sn) is the supernatant fraction obtained after the n$^{th}$ centrifugation), and a step of allowing a fluid including at least a part of the supernatant fraction (S0) and the supernatant fractions (S1) to (Sn) of the n times to flow in a flow cell and imaging the fluid flowing in the flow cell.

One aspect of the present invention is the method of acquiring an image of biological particles, in which a part or all of the supernatant fraction (S0) and the supernatant fractions (S1) to (Sn) are mixed and a fluid including at least a part of the mixture is allowed to flow in the flow cell.

One aspect of the present invention is the method of acquiring an image of biological particles, in which the fluid is allowed to flow in the flow cell includes the colloidal solution.

One aspect of the present invention is the method of acquiring an image of biological particles, in which the fluid allowed to flow in the flow cell includes a fluid obtained by sieving the supernatant fraction (S0) with a sieve (C) having meshes smaller than meshes of the sieve (B) to acquire a fraction which does not pass through the sieve (C), and adding the colloidal solution to the fraction.

One aspect of the present invention is the method of acquiring an image of biological particles, in which the fluid allowed to flow in the flow cell includes a fluid obtained by sieving the supernatant fractions (S1) to (Sn) with a sieve (C) having meshes smaller than meshes of the sieve (B) to acquire a fraction which does not pass through the sieve (C), and adding the colloidal solution to the fraction.

One aspect of the present invention is the method of acquiring an image of biological particles, further including a step of recovering the fluid for which the imaging is finished.

One aspect of the present invention is the method of acquiring an image of biological particles, in which the biological particles are meiofauna.

One aspect of the present invention is the method of acquiring an image of biological particles, in which the colloidal solution is colloidal silica.

One aspect of the present invention is the method of acquiring an image of biological particles, in which the biological particles have been stained with a dye.

One aspect of the present invention is an apparatus for pretreating a sample including biological particles, including a sieving section which is provided with a sieve (A) having meshes of 250 to 1000 µm and a sieve (B) having meshes of 32 to 63 µm, and which performs sieving of a sample including biological particles as a detection target to acquire a fraction (1b) which passes through the sieve (A) and does not pass through the sieve (B), a colloidal solution addition section for adding a colloidal solution to the fraction (1b) acquired by the sieving section, a centrifugation section for subjecting the fraction (1b) to which the colloidal solution was added to centrifugation, and a supernatant fraction-acquiring section for acquiring a supernatant fraction after the centrifugation in the centrifugation section.

One aspect of the present invention is a biological particle image-acquiring apparatus, including a sieving section which is provided with a sieve (A) and a sieve (B) having meshes smaller than meshes of the sieve (A), and which performs sieving of a sample including biological particles as a detection target to acquire a fraction (1b) which passes through the sieve (A) and does not pass through the sieve (B), a colloidal solution addition section for adding a colloidal solution to the fraction (1b) acquired by the sieving section, a centrifugation section for subjecting the fraction (1b) to which the colloidal solution was added to centrifugation, a supernatant fraction-acquiring section for acquiring a supernatant fraction after the centrifugation in the centrifugation section, and an imaging section which is provided with a flow cell and a camera and which allows a fluid including at least a part of the supernatant fraction acquired by the supernatant fraction-acquiring section to flow in the flow cell and images the fluid flowing in the flow cell with the camera, in which the sieve (A) has meshes smaller than whichever is larger of either of an inner diameter of the flow cell in a width direction and a depth direction.

One aspect of the present invention is the biological particle image-acquiring apparatus, in which the sieve (B) has meshes having a size upon which the camera is able to focus which is defined by an inner diameter of the flow cell in a depth direction and a depth of focus of the camera.

One aspect of the present invention is the biological particle image-acquiring apparatus, in which the sieve (B) has meshes which are a minimum value or more of a particle diameter upon which the camera is able to focus and which is defined by an inner diameter of the flow cell in a depth direction and a depth of focus of the camera.

One aspect of the present invention is a biological particle image-acquiring apparatus, in which the sieve (A) has meshes of 250 to 1000 µm and the sieve (B) has meshes of 32 to 63 µm.

Advantageous Effects of Invention

According to the present invention, since biological particles as a detection target are concentrated by sieving and then a colloidal solution is further added thereto to perform centrifugation, it is possible to efficiently concentrate the biological particles as the detection target even in a case where a large amount of sediment particles are present in the original sample. Therefore, a technique capable of quickly analyzing biological particles can be provided.

DESCRIPTION OF EMBODIMENTS

<Method of Pretreating Sample Including Biological Particles>

First Embodiment

In one embodiment, the present invention relates to a method of pretreating a sample including biological particles, the method including a step of acquiring a fraction (1b) which passes through a sieve (A) having meshes of 250 to 1000 µm and does not pass through a sieve (B) having meshes of 32 to 63 µm by sieving a sample including biological particles as a detection target (hereinafter referred to as "step (I)"), and a step of adding a colloidal solution having a density of 1.10 to 2.45 g/cm³ to the fraction (1b), subjecting the resultant solution to centrifugation, and acquiring a supernatant fraction (S0) after the centrifugation (hereinafter referred to as "step (II)").

A description will be given of an outline of the method of the present embodiment with reference to FIGS. 1a to 1c.

Figure 1:
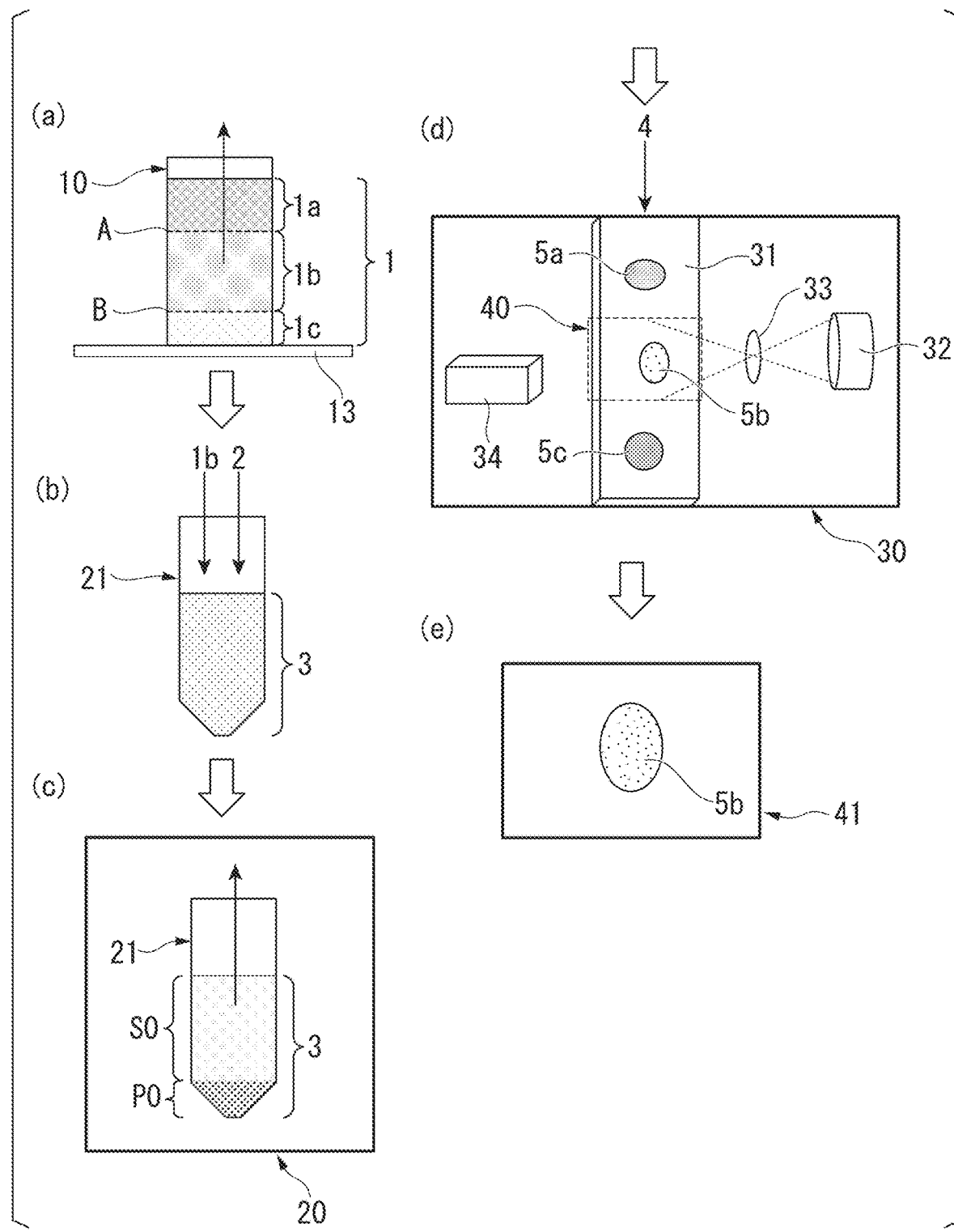
FIG. 1 schematically shows a method of acquiring an image of biological particles according to one embodiment of the present invention.

First, a sample 1 including biological particles as a detection target is sieved using a sieve (A) having meshes of 250 to 1000 µm and a sieve (B) having meshes of 32 to 63 µm, and a fraction (1b) which passes through the sieve (A) and does not pass through the sieve (B) is acquired (FIG. 1a; step (I)).

Next, a colloidal solution 2 having a density of 1.10 to 2.45 g/cm³ is added to the fraction (1b) and stirred appropriately (FIG. 1b). Thereafter, a mixture 3 including the fraction (1b) and the colloidal solution 2 is subjected to centrifugation to acquire a supernatant fraction (S0) (FIG. 1c) (the above is step (II)).

A description will be given below of each step of the method of the present embodiment.

(Step (1))

Step (1) is a step of acquiring a fraction (1b) which passes through a sieve (A) having meshes of 250 to 1000 µm and does not pass through a sieve (B) having meshes of 32 to 63 µm by sieving a sample including biological particles as a detection target.

In step (1), the sample 1 including biological particles as a detection target is sieved. In the method of the present embodiment, the biological particles to be a detection target are biological particles which pass through a sieve (A) having meshes of 250 to 1000 µm and do not pass through a sieve (B) having meshes of 32 to 63 µm. Examples of such biological particles include meiofauna. The biological particles to be a detection target may be particles which pass through a sieve having meshes of 250 to 500 µm and do not pass through a sieve having meshes of 32 to 63 µm, or may be particles which pass through a sieve having meshes of 250 µm and do not pass through a sieve having meshes of 63 µm.

According to the method of the present embodiment, it is possible to acquire images having sufficient image quality to classify the organism species, even with a sample including a lot of sediment. Therefore, the biological particles to be a detection target may be organisms inhabiting the sediment. Examples of such organisms include benthic organisms or the like which live on the seafloor, lake bottoms, river bottoms, and the like. From this viewpoint also, meiofauna, which are benthic organisms, are suitable as the biological particles as a detection target.

The biological particles as a detection target for the method of the present embodiment may be the whole organism or a part of the organism. In addition, the biological particles may be dormant particles such as spores, eggs, and the like. In addition, the biological particles are not limited to living organisms, and may be dead organisms.

The sample 1 to be sieved according to the method of the present embodiment is not particularly limited as long as the sample 1 includes biological particles as a detection target. Examples of the sample 1 include samples or the like collected from an environment in which the biological particles as a detection target inhabit. In the method of the present embodiment, since the sample may include sediment, a sediment sample collected from the ocean floor, a lake bottom, a river bottom, or the like may be used as the sample 1. For example, in a case where the biological particles as a detection target are meiofauna, it is possible to use a sediment sample collected from the deep seafloor as the sample 1.

The sample 1 to be sieved according to the method of the present embodiment may be a sample collected from the environment as it is, or may be subjected to treatment such as fixation or dyeing. In a case where fixation of a sample is performed, it is possible to prevent decay of the sample. Therefore, it is preferable to fix the samples in a case where the collected samples are not to be used immediately. The fixation method is not particularly limited, and the fixation of the sample may be performed by a generally used method. For example, it is possible to fix using reagents such as formalin, ethanol, Lugol's solution, glutaraldehyde, RNAlater™ (Invitrogen), or the like, or by freezing. Examples of a suitable fixation method include formalin fixation.

In addition, in a case where the sample is subjected to a dyeing treatment, and then, an image of the biological particles in the pretreatment sample is acquired, it is possible to easily view the biological particles in the image. Therefore, the biological particles in the sample 1 are preferably dyed with a pigment or the like before sieving. The dyeing treatment method is not particularly limited, and the dyeing treatment for the sample may be performed using commonly used pigments or the like. For example, it is possible to perform the dyeing treatment using Rose Bengal, Congo Red, CellTracker™ Green (ThermoFisher Scientific), or the like. Examples of suitable dyeing treatment methods include Rose Bengal dyeing.

At least two sieves are used for sieving the sample 1. One is a sieve (A) having meshes of 250 to 1000 μm and the other is a sieve (B) having meshes of 32 to 63 μm. The sieve (A) having meshes of 250 to 1000 μm is used to remove fractions which do not pass through the sieve from the sample 1. In addition, a sieve (B) having meshes of 32 to 63 μm is used to remove the fraction which passes through the sieve from the sample 1. Then, in step (I), from the sample 1, a fraction which passes through the sieve (A) having meshes of 250 to 1000 μm and does not pass through a sieve (B) having meshes of 32 to 63 μm is acquired. Due to this, it is possible to remove sediment having a large diameter included in the sample 1 and to remove particles smaller than the biological particles as a detection target.

The sieves (A) and (B) are not particularly limited as long as the meshes are in the above ranges and commonly used sieves may be used. In addition, the size of the meshes may be varied within the above ranges according to the size of the biological particles as a detection target. Narrowing the range of meshes of the fraction (1b) acquired by sieving makes it possible to more efficiently image the biological particles as a detection target in a subsequent imaging step.

For example, in a case where the biological particles as a detection target are meiofauna, approximately 98% or more of the individuals are present in the sieve fraction of 38 to 500 μm, approximately 83% or more of the individuals are present in the sieve fraction of 38 to 250 μm, and approximately 75% of the individuals are present in the sieve fraction of 63 to 250 μm (refer to Table 1). Therefore, in step (I), a fraction which passes through a sieve of 250 to 500 μm and does not pass through a sieve of 32 to 63 μm may be acquired, a fraction which passes through a sieve of 250 to 500 μm and does not pass through a sieve of 38 to 63 μm may be acquired, and a fraction which passes through a 250 μm sieve and does not pass through a 63 μm sieve may be acquired.

The method of sieving in this step is not particularly limited and the sieving may be performed using a generally used method. For example, as shown in FIG. 1a, the sieve (A) having meshes of 250 to 1000 μm and the sieve (B) having meshes of 32 to 63 μm are installed in a container 10, and the sample 1 may be sieved by being poured over the sieve (A). Due to this, the sample 1 is sieved into a fraction (1a) which does not pass through the sieve (A) having meshes of 250 to 1000 μm, a fraction (1b) which passes through the sieve (A) having meshes of 250 to 1000 μm and does not pass through the sieve (B) having meshes of 32 to 63 μm, and a fraction (1c) which passes through the sieve (B) having meshes of 32 to 63 μm.

In the example shown in FIG. 1a, the container 10 is installed on a shaker 13 and sieving is performed while shaking with the shaker 13. Sieving while shaking makes it possible to shorten the time required for sieving.

After sieving, for example, it is possible to acquire the fraction (1b) by removing the sieve (A) including the particles trapped by the sieve (A) and obtaining the sieve (B) including the particles trapped by the sieve (B).

In the example of FIG. 1a, the sieve (A) and the sieve (B) are installed in the container 10, but the method of installing the sieve (A) and the sieve (B) is not limited thereto. For example, a container for gathering a fraction (1a) which does not pass through a sieve (A), a container for gathering a fraction (1b) which passes through the sieve (A) and does not pass through the sieve (B), a container for gathering a fraction (1c) which passes through the sieve (B), may be set as separate containers, and the sieve (A) may be installed in the container which gathers the fraction (1a) which does not pass through the sieve (A) and the sieve (B) may be installed in the container which gathers the fraction (1b) which passes through the sieve (A) and does not pass through the sieve (B). In such a case, it is possible to acquire the fraction (1b) by sieving the sample 1 and then acquiring a container in which the sieve (B) is installed.

(Step (II))

Step (II) is a step in which a colloidal solution having a density of 1.10 to 2.45 g/cm$^3$ is added to the fraction (1b), centrifugation is performed, and the supernatant fraction (S0) after the centrifugation is acquired.

In step (II), the colloidal solution 2 having a density of 1.10 to 2.45 g/cm$^3$ is added to the fraction (1b) (FIG. 1b). In the example of FIG. 1b, a fraction (1b) is placed in a centrifuge tube 21 and the colloidal solution 2 is added thereto to acquire the mixture 3 including the fraction (1b) and the colloidal solution 2. The colloidal solution 2 is not particularly limited as long as the colloidal solution 2 has a density of 1.10 to 2.45 g/cm$^3$. The density of biological particles included in the fraction 1b is approximately 1.0 to 1.2 g/cm$^3$ and the density of the sediment particles is approximately 2.5 to 2.8 g/cm$^3$. Therefore, adding the colloidal solution 2 having a density of 1.10 to 2.45 g/cm$^3$ to the fraction 1b makes it possible to separate the biological particles and sediment into a supernatant fraction and precipitate when centrifugation is performed. The density of the colloidal solution 2 is preferably 1.10 to 2.00 g/cm$^3$, and more preferably 1.10 to 1.50 g/cm$^3$.

In addition, the colloidal solution 2 preferably has a pH of 4.0 to 11.0. If the pH is within this range, it is possible to avoid adverse effects on the biological particles.

Examples of the colloidal solution 2 usable in step (II) include colloidal silica. In addition, as the colloidal solution 2, a commercially available solution may be used. For example, it is possible to use Ludox (registered trademark) HS-40 (Sigma Aldrich; density 1.3 g/cm$^3$, pH 9.5-10.3), Percoll (registered trademark) (GE Healthcare; density 1.13 g/cm$^3$, pH 9.0), RNAlater™ (Invitrogen; 1.25 g/cm$^3$, pH 5.0), and the like, as the colloidal solution 2.

The amount of the colloidal solution 2 to be added is not particularly limited and may be any amount as long as it is possible to suspend the fraction (1b). For example, it is possible to set the addition amount of the colloidal solution 2 such that the sample 1:colloidal solution 2=1:1 to 5 as the volume ratio with the sample 1 before sieving.

After adding the colloidal solution 2 to the fraction (1b), the mixture 3 including the fraction (1b) and the colloidal solution 2 is subjected to centrifugation by a centrifuge 20 (FIG. 1c). Due to this, the mixture 3 is separated into a supernatant fraction (S0) and a precipitate (P0). The supernatant fraction (S0) includes an abundance of biological particles as a detection target, and the precipitate (P0) includes an abundance of sediment.

It is possible to appropriately select the conditions for centrifugation in this step depending on the type of biological particles as a detection target. For example, in a case where the detection target is meiofauna, examples of the conditions for centrifugation include 600 to 1000 G, preferably 700 to 900 G, more preferably 750 to 850 G, and particularly preferably 800 G.

In addition, the time for centrifugation may be, for example, 3 to 30 minutes, preferably 5 to 20 minutes, more preferably 8 to 15 minutes, and particularly preferably 10 minutes.

After centrifugation, the supernatant fraction (S0) may be acquired using a pipette or the like.

It is possible to use the sample prepared by the method of pretreating a sample of the present embodiment, for example, as a sample for acquiring images of biological particles. For example, in an imaging apparatus provided with a flow cell as shown in FIG. 1d described below, it is possible to suitably use such a sample as a sample to be introduced in a flow cell.

According to the method of pretreating a sample of the present embodiment, even for samples containing a lot of sediment, it is possible to prepare a sample suitable for acquiring images of biological particles by efficiently removing the sediment. In addition, in a case where the sample prepared by the method of pretreating a sample of the present embodiment includes a colloidal solution, when the sample is introduced into a flow cell to acquire an image of the biological particles, it is possible to prevent settling of the biological particles in the flow cell and to prevent the flow cell from becoming clogged with biological particles.

In addition, the sample prepared by the method of pretreating a sample of the present embodiment can be used for various analyses such as genome analysis.

(Optional Steps)

The method of the present embodiment may further include a step of preparing a supernatant fraction (S0) in addition to step (I) and step (II) described above.

Examples of a step of preparing the supernatant fraction (S0) include a step of adding the colloidal solution 2 to the supernatant fraction (S0). The supernatant fraction (S0) usually includes the colloidal solution 2, but further adding the colloidal solution 2 makes it possible to adjust the buoyancy of the biological particles in the sample.

In addition, examples of a step of preparing the supernatant fraction (S0) also include a step in which a fraction which does not pass through the sieve (C) is acquired by sieving with a sieve (C) having meshes smaller than the meshes of the sieve (B) and, the colloidal solution 2 is added to the fraction. Sieving with a sieve (C) having meshes smaller than the meshes of the sieve (B) makes it possible to remove excess colloidal particles and concentrate the target biological particles. In addition, using a sieve having meshes smaller than the meshes of the sieve (B) makes it possible to reduce the loss of biological particles as a detection target. The meshes of the sieve (C) are not particularly limited as long as the meshes are smaller than the meshes of the sieve (B) used in step (I) and examples thereof include 30 to 63 μm.

The colloidal solution 2 to be used in this step may be the same as used in step (II).

Second Embodiment

In one embodiment, the present invention is a method of pretreating a sample for acquiring an image of biological particles, the method including a step of acquiring a fraction (1b) which passes through a sieve (A) having meshes of 250 to 1000 μm and does not pass through a sieve (B) having meshes of 32 to 63 μm by sieving a sample including biological particles as a detection target (hereinafter referred to as "step I"), a step in which a colloidal solution having a density of 1.10 to 2.45 g/cm$^3$ is added to the fraction (1b), centrifugation is performed, and the supernatant fraction (S0) after the centrifugation is acquired (hereinafter referred to as "step II"), and a step of performing suspending a precipitate (Pn−1) after centrifugation in the colloidal solution to perform centrifugation, and acquiring a supernatant fraction (Sn) after the centrifugation, n times (n is an integer of 1 or more, the precipitate (Pn−1) is a precipitate obtained after the (n−1)$^{th}$ centrifugation, and the supernatant fraction (Sn) is the supernatant fraction obtained after the n$^{th}$ centrifugation) (hereinafter referred to as "step II'").

A description will be given of an outline of the method of the present embodiment with reference to FIGS. 1a to 1c, FIGS. 2a to 2c, and FIGS. 2a-n to c-n.

First, the sample 1 including biological particles as a detection target is sieved using a sieve (A) having meshes of 250 to 1000 μm and a sieve (B) having meshes of 32 to 63 μm to acquire a fraction (1b) which passes through the sieve (A) having meshes of 250 to 1000 μm and does not pass through the sieve (B) having meshes of 32 to 63 μm (FIG. 1a; step (I)).

Next, the colloidal solution 2 having a density of 1.10 to 2.45 g/cm$^3$ is added to fraction (1b) and stirred appropriately (FIG. 1b). Thereafter, the mixture 3 including the fraction (1b) and the colloidal solution 2 is subjected to centrifugation to acquire a supernatant fraction (S0) (FIG. 1c) (the above is step (11)).

Figure 2:
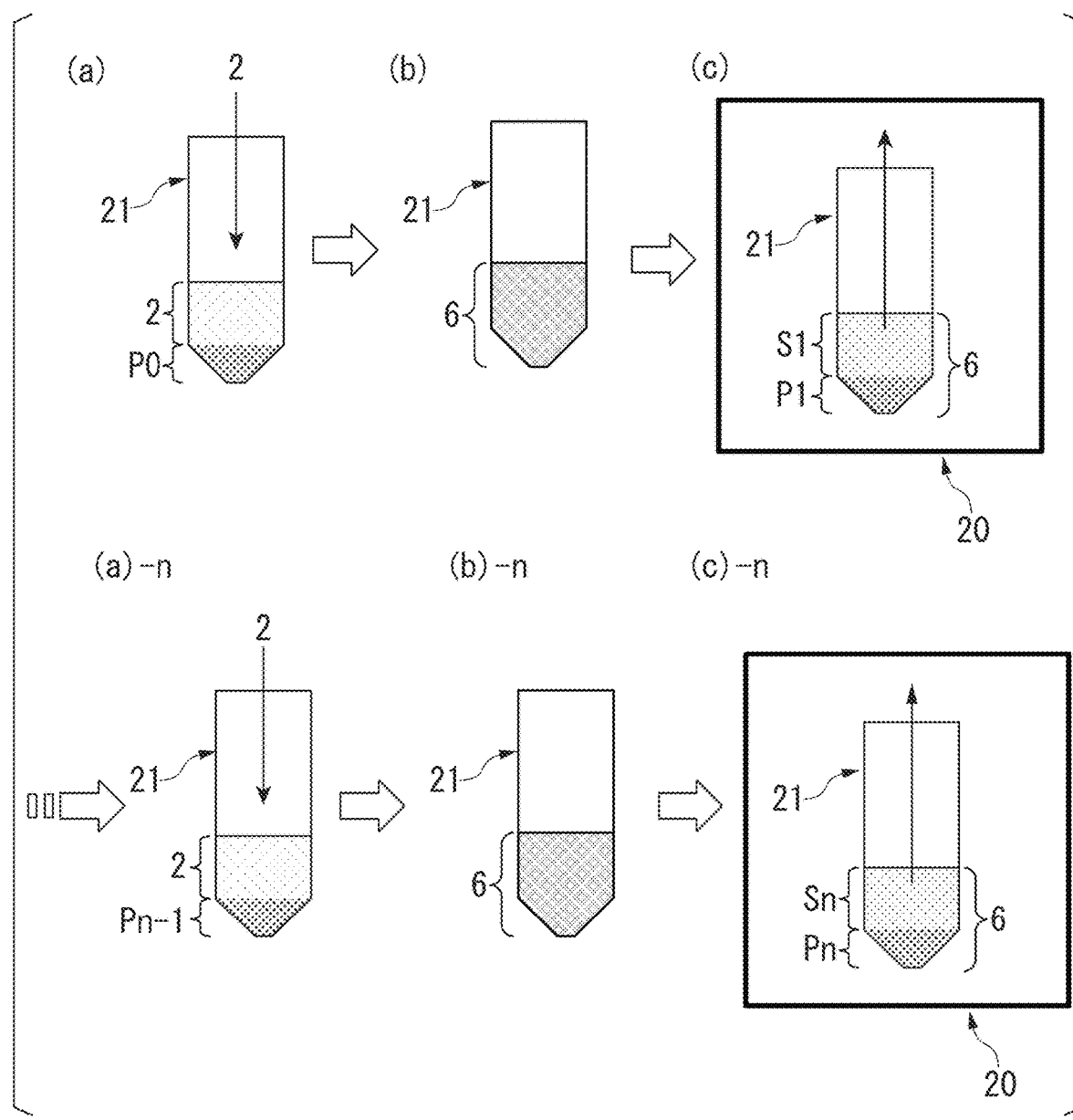
FIG. 2 shows an example of steps in a method of acquiring an image of biological particles according to one embodiment of the present invention.

Next, the colloidal solution 2 is added to the precipitate (P0) after centrifugation (FIG. 2a), and the precipitate (P0) is suspended in the colloidal solution 2 to create a suspension 6 (FIG. 2b). Then, the suspension 6 is subjected to centrifugation to acquire a supernatant fraction (S1) (FIG. 2c). In this manner, the supernatant fractions (S1) to (Sn) after centrifugation n times are acquired (FIGS. 2a-n to c-n)) (the above is step (11)).

A description will be given below of each step of the method of the present embodiment.

(Step (I) and Step (II))

Step (I) and step (II) are the same as step (I) and step (II) in the method of the first embodiment described above. Therefore, explanation thereof is omitted.

(Step (II'))

Step (II') is a step of suspending a precipitate (Pn−1) after centrifugation in the colloidal solution to perform centrifugation and acquiring a supernatant fraction (Sn) after the centrifugation, n times (n is an integer of 1 or more, the precipitate (Pn−1) is a precipitate obtained after the (n−1)$^{th}$ centrifugation, and the supernatant fraction (Sn) is the supernatant fraction obtained after the n$^{th}$ centrifugation).

In step (II'), the colloidal solution 2 is added to the precipitate (P0) obtained by centrifugation in step (II) (FIG. 2a). The same colloidal solution 2 as used in step (II) may be used. Then, the precipitate (P0) is suspended in the colloidal solution 2 to obtain the suspension 6 (FIG. 2b). When the suspension 6 is subjected to centrifugation, the suspension 6 is separated into a supernatant fraction (S1) and a precipitate (P1) (FIG. 2c). Biological particles remaining in the precipitate (P0) transfer to the supernatant fraction (S1) while sediment remains in the precipitate (P1).

The centrifugation conditions described above may be the same as or different from those of the centrifugation in step (II), but are preferably the same. After centrifugation, a supernatant fraction (S1) may be acquired using a pipette or the like.

The colloidal solution 2 is again added to the precipitate (P1) obtained by the centrifugation described above, as necessary, and is suspended and subjected to centrifugation. Then, a supernatant fraction (S2) obtained after centrifugation is acquired. When the supernatant fraction obtained by the $n^{th}$ centrifugation in this manner is the supernatant fraction (Sn) and the precipitate obtained by the $n^{th}$ centrifugation is the precipitate (Pn), it is possible to acquire the supernatant fractions (S1) to (Sn) by adding the colloidal solution 2 to the precipitate (Pn−1), carrying out suspension, and performing centrifugation n times.

In this step, n may be an integer of 1 or more, and the number of times of centrifugation is not particularly limited. As the number of times of centrifugation is increased (as n is increased), it is possible to increase the recovery rate of biological particles remaining in the precipitate (Pn). Normally, it is possible for n to be an integer of 1 to 5, and n may be an integer of 1 to 3, for example, n can be 2 or 3.

The added amount of the colloidal solution 2 to the precipitate (Pn−1) is not particularly limited as long as it is an amount in which it is possible to suspend the precipitate (Pn−1). Depending on the amount of precipitate (Pn−1), an appropriate amount of colloidal solution 2 may be added thereto to suspend the precipitate (Pn−1). Examples of the amount of the colloidal solution 2 to be added include precipitate (Pn−1):colloidal solution 2=2:3, or the like as the volume ratio with the precipitate (Pn−1).

The sample pretreated by the method of the present embodiment usually includes the colloidal solution 2. The supernatant fraction (S0) obtained in step (II) and the supernatant fractions (S1) to (Sn) obtained in step (II') are mixed partially or wholly and it is possible to use the result for image acquisition, analysis, or the like as described below.

It is possible to use the sample prepared by the method of pretreating a sample of the present embodiment as a sample for acquiring an image of biological particles in the same manner as the sample prepared by the method of the first embodiment.

According to the method of the present embodiment, it is possible to efficiently remove sediment to prepare a sample suitable for acquiring images of biological particles, even for samples containing a lot of sediment. In addition, in step (II'), since the colloidal solution is added to the precipitate obtained by centrifugation and further centrifugation is carried out, it is possible to recover the biological particles even in a case where the biological particles remain in the precipitate.

In addition, it is possible to subject the sample prepared by the method of pretreating a sample of the present embodiment to various analyses such as genome analysis in the same manner as the sample prepared by the method of the first embodiment.

(Optional Steps)

In the method of the present embodiment, a step of preparing the supernatant fraction (S0) and the supernatant fractions (S1) to (Sn) may be included in addition to the above steps (I), (II), and (II').

Examples of a step of preparing the supernatant fraction (S0) and supernatant fractions (S1) to (Sn) include a step of adding the colloidal solution 2 to the supernatant fraction (S0) and supernatant fractions (S1) to (Sn). Usually, the supernatant fraction (S0) and the supernatant fractions (S1) to (Sn) include the colloidal solution 2, but further adding the colloidal solution 2 makes it possible to adjust the buoyancy of the biological particles in the sample.

The colloidal solution 2 may be added individually to each of the supernatant fraction (S0) and the supernatant fractions (S1) to (Sn), and may be added to a part or the whole of a mixture of the supernatant fraction (S0) and the supernatant fractions (S1) to (Sn). In a case where the colloidal solution 2 is individually added to each of the supernatant fraction (S0) and the supernatant fractions (S1) to (Sn), the supernatant fraction (S0) and supernatant fractions (S1) to (Sn) may be mixed in part or in whole after the addition of the colloidal solution 2.

In addition, examples of a step of preparing the supernatant fraction (S0) and the supernatant fractions (S1) to (Sn) also include a step of acquiring a fraction which does not pass through the sieve (C) by sieving with the sieve (C) having meshes smaller than the meshes of the sieve (B) and adding the colloidal solution 2 to the fraction. Sieving with a sieve (C) having meshes smaller than the meshes of the sieve (B) makes it possible to remove excess colloidal particles to concentrate the biological particles which are the target. In addition, using a sieve having meshes smaller than the meshes of the sieve (B) makes it possible to reduce the loss of the biological particles as a detection target. The meshes of the sieve (C) are not particularly limited as long as the meshes are smaller than the meshes of the sieve (B) used in step (I) and examples thereof include 30 to 63 μm.

The colloidal solution 2 to be used in this step may be the same as used in step (II).

The sieving using the sieve (C) may be performed individually for each of the supernatant fraction (S0) and the supernatant fractions (S1) to (Sn), or may be performed for a part or the whole of a mixture of the supernatant fraction (S0) and the supernatant fractions (S1) to (Sn). In a case where the sieving and the addition of the colloidal solution 2 are performed individually for each of the supernatant fraction (S0) and the supernatant fractions (S1) to (Sn), after the sieving and addition of the colloidal solution 2, a part or the whole of the obtained sample may be mixed.

<Method of Acquiring Image of Biological Particles>

First Embodiment

In one embodiment, the present invention is a method of acquiring an image of biological particles including a step of acquiring a fraction (1b) which passes through a sieve (A) having meshes of 250 to 1000 μm and does not pass through a sieve (B) having meshes of 32 to 63 μm by sieving a sample including biological particles as a detection target (hereinafter referred to as "step I"), a step in which a colloidal solution having a density of 1.10 to 2.45 g/cm³ is added to the fraction (1b), centrifugation is performed, and the supernatant fraction (S0) after the centrifugation is acquired (hereinafter referred to as "step II"), and a step of allowing a fluid including at least a part of the supernatant fraction (S0) to flow in a flow cell and imaging the fluid flowing in the flow cell (hereinafter referred to as "step III").

A description will be given of the outline of the method of the present embodiment with reference to FIGS. 1a to 1e.

First, the sample 1 including biological particles as a detection target is sieved using a sieve (A) having meshes of 250 to 1000 μm and a sieve (B) having meshes of 32 to 63 μm, and a fraction (1b) which passes through the sieve (A) having meshes of 250 to 1000 μm and does not pass through the sieve (B) having meshes of 32 to 63 μm is acquired (FIG. 1a; step (1)).

Next, the colloidal solution 2 having a density of 1.10 to 2.45 g/cm$^3$ is added to the fraction (1b) and stirred appropriately (FIG. 1b). Thereafter, the mixture 3 including the fraction (1b) and the colloidal solution 2 is subjected to centrifugation to acquire a supernatant fraction (S0) (FIG. 1c) (the above is step (II)).

Next, while allowing a fluid 4 including at least a part of the supernatant fraction (S0) to flow in a flow cell 31, the flow cell 31 in a frame 40 is imaged by a camera 32 (FIG. 1d; step (III)). In the example of FIG. 1d, imaging is performed via an objective lens 33.

Due to this, at the time of imaging, it is possible to acquire an image 41 of the biological particles 5b present in the frame 40.

A description will be given of each step of the method of the present embodiment below.

(Step (I) and Step (II))

Step (I) and step (II) are the same as step (I) and step (II) in the "<Method of Pretreating Sample Including Biological Particles>" described above. Therefore, explanation thereof is omitted.

(Step (III))

Step (III) is a step of allowing a fluid including at least a part of the supernatant fraction (S0) to flow in the flow cell and imaging the fluid flowing in the flow cell.

In step (III), first, the fluid 4 including at least a part of the supernatant fraction (S0) is allowed to flow in the flow cell 31. The fluid 4 flowing in the flow cell 31 preferably includes the colloidal solution 2. Including the colloidal solution 2 in the fluid 4 makes it possible to prevent precipitation of the biological particles as the detection target and to prevent the clogging of the flow cell 31 with the biological particles.

Since the supernatant fraction (S0) usually includes the colloidal solution 2, the supernatant fraction (S0) may be allowed to flow as the fluid 4 in the flow cell 31 as it is. In addition, a supernatant fraction (S0) to which the colloidal solution 2 is further added may be allowed to flow as the fluid 4 in the flow cell 31.

In addition, the supernatant fraction (S0) may be subjected to a treatment such as sieving to acquire a predetermined fraction, and thereby the fluid 4 may be prepared to be allowed to flow in the flow cell 31. For example, the fluid 4 may be obtained by removing excess colloidal particles from the supernatant fraction (S0) using a sieve (C) having meshes smaller than the meshes of the sieve (B), acquiring a fraction which does not pass through the sieve (C), and adding the colloidal solution 2 to the fraction. That is, the fluid 4 may include a fluid obtained by sieving the supernatant fraction (S0) with a sieve (C) having meshes smaller than the meshes of the sieve (B) to acquire a fraction which does not pass through the sieve (C), and adding the colloidal solution 2 to the fraction. Sieving with a sieve (C) having meshes smaller than the meshes of the sieve (B) makes it possible to remove excess colloidal particles to concentrate the biological particles as a target and to perform the imaging efficiently. In addition, using a sieve having meshes smaller than the meshes of the sieve (B) makes it possible to reduce the loss of the biological particles as a detection target. The meshes of the sieve (C) are not particularly limited as long as the meshes are smaller than the meshes of the sieve (B) used in step (I) and examples thereof include 30 to 63 μm.

In this step, while allowing the fluid 4 including at least a part of the supernatant fraction (S0) prepared as described above to flow in the flow cell 31, the fluid 4 flowing in the flow cell 31 is imaged. In the example of FIG. 1d, the fluid 4 flowing in the flow cell 31 is imaged by the camera 32 installed in an imaging apparatus 30 via the objective lens 33. In the example of FIG. 1d, the imaging portion (frame 40) of the flow cell 31 is irradiated with light by a light source 34.

The flow cell 31 preferably has high transparency to enable imaging of the fluid 4 flowing inside. Although the shape of the flow cell 31 is not particularly limited, the shape of the flow cell 31 is preferably a shape where the surface imaged by the camera 32 is a flat surface. Examples of the shape of the flow cell 31 include a rectangular parallelepiped. The size of the flow cell 31 is not particularly limited and is able to be appropriately selected according to the biological particles as the detection target. For example, in a case where the detection target is meiofauna, it is possible to use the flow cell 31 having an inner diameter of 150 to 500 μm in the depth direction with respect to the imaging plane of the camera 32. The inner diameter is preferably 200 to 400 μm, and more preferably 250 to 350 μm.

Herein, the term "inner diameter in the depth direction" of the flow cell means the inner diameter of the flow cell in the direction orthogonal to the imaging plane. In addition, the term "inner diameter in the width direction" of the flow cell means the inner diameter of the flow cell in a direction parallel to the imaging surface.

The method of introducing the fluid 4 into the flow cell 31 is not particularly limited. For example, the introduction may be carried out using pipetting or the like, or may be performed by connecting a tube to the upstream side of the flow cell 31 and bringing the upstream end of the tube into contact with the fluid 4 in a container or the like to suction up the fluid 4. In addition, it is possible to create the flow of the fluid 4 in the flow cell 31, for example, by connecting a pump to the downstream side of the flow cell 31 via a tube or the like and operating the pump, or the like. In addition, the inside of the flow cell 31 (in a case where a tube is connected to the upstream side of the flow cell 31, the inside of the tube as well) is preferably filled with the colloidal solution 2 before introducing the fluid 4 into the flow cell 31.

In the example of FIG. 1d, imaging is performed by the camera 32 via the objective lens 33. Using the objective lens 33 makes it possible to acquire an enlarged image of the biological particles. The magnification of the objective lens 33 is not particularly limited and is able to be appropriately selected according to the biological particles as the detection target. For example, in a case where the detection target is meiofauna, it is possible to use an objective lens with a magnification of 1 to 20 times, and the magnification is preferably 2 to 10 times, and the magnification is more preferably 2 to 5 times. Imaging may be performed without using the objective lens 33 and the image enlargement processing may be performed after imaging.

In addition, in the example of FIG. 1d, the light source 34 irradiates the imaging portion with light to perform imaging. Performing the imaging by irradiating the imaging portion with light makes it possible to acquire a clearer image. The light source 34 may intermittently irradiate light in accordance with the imaging or may constantly irradiate light. The light to be irradiated is not particularly limited, but is preferably visible light. In step (I), in a case where a sample dyed with a fluorescent dye is used as the sample 1, the sample may be irradiated with light having a wavelength which excites the fluorescent dye.

In addition, in the example of FIG. 1d, the camera 32 acquires the image of the fluid 4 present in the frame 40 on the flow cell 31. The image imaged by the camera 32 may be a still image or may be a moving image. In a case of imaging a still image, the camera 32 preferably performs imaging at predetermined time intervals. The imaging interval may be appropriately selected according to the flow velocity of the fluid 4 flowing in the flow cell 31. It is possible for the imaging interval to be, for example, 5 to 50 times/second or the like.

In the imaging apparatus 30 having the above-described configuration, when the fluid 4 including at least a part of the supernatant fraction (S0) is allowed to flow in the flow cell 31, biological particles 5a to 5c included in the fluid 4 move in the flow cell 31 according to the flow of the fluid 4. Meanwhile, the camera 32 continuously acquires the images of the frame 40 on the flow cell 31. Therefore, when the biological particles 5a to Sc move into the frame 40, images of the biological particles 5a to 5c are imaged. In the example of FIG. 1d, images of the biological particles 5b are imaged. As a result, it is possible to acquire the image 41 of the biological particles 5b (FIG. 1e).

It is possible to use images of biological particles acquired by the method of the present embodiment for analysis for classifying organism species. For example, classifying images acquired by the method of the present embodiment by visual observation or an image analysis program or the like makes it possible to analyze biota quickly as compared with the methods using microscopes in the related art.

According to the method of the present embodiment, since it is possible to remove sediment by a sieving treatment and a centrifugation treatment, it is possible to efficiently acquire images of biological particles even for samples including sediment. In addition, in a case where the fluid flowing in a flow cell includes a colloidal solution, it is possible to prevent precipitation of the biological particles in the flow cell and to prevent the clogging of the flow cell with biological particles.

(Optional Step)

In addition to the above steps (I) to (III), the method of the present embodiment may further include a step of recovering the fluid 4 for which the imaging is finished. Recovering the fluid 4 for which the imaging is finished makes it possible to carry out further analysis of the biological particles included in the fluid 4.

In a case of recovering the fluid 4 which the imaging is finished, for example, a tube or the like may be connected to the downstream side of the flow cell 31 and the downstream end of the tube may be installed in a sealed container or the like. If a pump or the like is connected to the sealed container so as to discharge the air in the sealed container, it is possible to create a flow of the fluid 4 in the flow cell 31, and furthermore, it is possible to recover the fluid 4 for which the imaging is finished in the sealed container.

The biological particles included in the fluid 4 recovered as described above are not crushed by a pump or the like and are hardly damaged. Therefore, it is possible to use the biological particles for further analysis.

Second Embodiment

In one embodiment, the present invention is a method of acquiring an image of biological particles including a step of acquiring a fraction (1b) which passes through a sieve (A) having meshes of 250 to 1000 μm and does not pass through a sieve (B) having meshes of 32 to 63 μm by sieving a sample including biological particles as a detection target (hereinafter referred to as "step I"), a step in which a colloidal solution having a density of 1.10 to 2.45 g/cm$^3$ is added to the fraction (1b), centrifugation is performed, and the supernatant fraction (S0) after the centrifugation is acquired (hereinafter referred to as "step II"), and a step of performing suspending a precipitate (Pn−1) after centrifugation in the colloidal solution to perform centrifugation, and acquiring a supernatant fraction (Sn) after the centrifugation, n times (n is an integer of 1 or more, the precipitate (Pn−1) is a precipitate obtained after the $(n-1)^{th}$ centrifugation, and the supernatant fraction (Sn) is the supernatant fraction obtained after the $n^{th}$ centrifugation) (referred to below as "step II'"), a step of allowing a fluid including at least a part of the supernatant fraction (S0) and the supernatant fractions (S1) to (Sn) of the n times to flow in the flow cell and imaging the fluid flowing in the flow cell (hereinafter referred to as "step III").

A description will be given of the outline of the method of the present embodiment with reference to FIGS. 1a to 1e, FIGS. 2a to c, and FIGS. 2a-n to c-n.

First, the sample 1 including biological particles as a detection target is sieved using a sieve (A) having meshes of 250 to 1000 μm and a sieve (B) having meshes of 32 to 63 μm, and a fraction (1b) which passes through the sieve (A) having meshes of 250 to 1000 μm and does not pass through the sieve (B) having meshes of 32 to 63 μm is acquired (FIG. 1a; step (I)).

Next, the colloidal solution 2 having a density of 1.10 to 2.45 g/cm$^3$ is added to the fraction (1b) and stirred appropriately (FIG. 1b). Thereafter, the mixture 3 including the fraction (1b) and the colloidal solution 2 is subjected to centrifugation to acquire a supernatant fraction (S0) (FIG. 1c) (the above is step (II)).

Next, the colloidal solution 2 is added to the precipitate (P0) after centrifugation (FIG. 2a), and the precipitate (P0) is suspended in the colloidal solution 2 to create the suspension 6 (FIG. 2b). Then, the suspension 6 is subjected to centrifugation to acquire a supernatant fraction (S1) (FIG. 2c). In this manner, the supernatant fractions (S1) to (Sn) after n times of centrifugation are acquired (FIGS. 2a-n to c-n)) (the above is step (II')).

Next, while allowing the fluid 4 including at least a part of the supernatant fraction (S0) and the supernatant fractions (S1) to (Sn) of the n times to flow in the flow cell 31, the flow cell 31 in the frame 40 is imaged by the camera 32 (FIG. 1d; step (HP)). In the example of FIG. 1d, imaging is performed via the objective lens 33. Due to this, at the time of imaging, it is possible to acquire the image 41 of the biological particles Sb present in the frame 40. A description will be given below of each step of the method of the present embodiment.

(Step (I), Step (II), and Step (II'))

Step (I), step (II) and step (II') are the same as step (I), step (II) and step (II') in the above "<Method of Pretreating Sample Including Biological Particles>". Therefore, explanation thereof will be omitted.

(Step (III'))

Step (III') is a step of allowing a fluid including at least a part of the supernatant fraction (S0) and the supernatant fractions (S1) to (Sn) of the n times to flow in a flow cell and imaging the fluid flowing in the flow cell.

In step (III'), the fluid 4 including at least a part of supernatant fractions (S0) obtained in step (II) and supernatant fractions (S1) to (Sn) obtained in step (II') is allowed to flow in the flow cell 31. A part or all of the supernatant fraction (S0) and the supernatant fraction (S1) to (Sn) may be mixed, and the fluid 4 may be prepared so as to include at least a part of the mixture. Preferably, all of the supernatant fraction (S0) and the supernatant fractions (S1) to (S0) are mixed and the fluid 4 is prepared to include at least a part of the mixture.

In the same manner as the method of the first embodiment, the fluid 4 flowing in the flow cell 31 preferably includes the colloidal solution 2. Since the supernatant fraction (S0) and the supernatant fractions (S1) to (Sn) usually include the colloidal solution 2, the supernatant fraction (S0) and the supernatant fractions (S1) to (Sn) may be allowed to flow into the flow cell 31 as the fluid 4 as it is. In addition, the supernatant fraction (S0) and the supernatant fractions (S1) to (Sn) to which the colloidal solution 2 is further added may be allowed to flow as the fluid 4 in the flow cell 31. In a case where a mixture of the supernatant fraction (S0) and the supernatant fractions (S1) to (Sn) is used, the colloidal solution 2 may be added to the mixture.

In addition, in the same manner as the method of the first embodiment, the fluid 4 may be prepared by further subjecting the supernatant fraction (S0) and the supernatant fractions (S1) to (Sn) to treatments such as sieving to acquire a predetermined fraction, and allowed to flow in the flow cell 31. For example, the fluid 4 may be obtained by sieving the supernatant fraction (S0) and the supernatant fractions (S1) to (Sn) using a sieve (C) having meshes smaller than meshes of the sieve (B), acquiring a fraction which does not pass through the sieve (C), and adding the colloidal solution 2 to the fraction. The sieving using the sieve (C) and the addition of the colloidal solution 2 may be performed individually for each of the supernatant fraction (S0) and the supernatant fractions (S1) to (Sn) respectively or may be performed on a mixture of part or all of the fraction (S0) and supernatant fractions (S1) to (Sn). In a case where the sieving and the addition of the colloidal solution 2 are performed individually for each of the supernatant fraction (S0) and the supernatant fractions (S1) to (Sn), a part or the whole of the obtained sample may be mixed after sieving and addition of the colloidal solution 2. That is, the fluid 4 may include a fluid in which the supernatant fraction (S0) and/or the supernatant fractions (S1) to (Sn) are sieved with a sieve (C) having meshes smaller than the meshes of the sieve (B) to acquire a fraction which does not pass through the sieve (C) and the colloidal solution 2 is added thereto. In addition, in a case where a mixture of the supernatant fraction (S0) and the supernatant fractions (S1) to (Sn) is used, the fluid 4 may be a fluid obtained by using the sieve (C) to sieve the mixture to acquire a fraction which does not pass through the sieve (C), and adding the colloidal solution 2 to the fraction. Sieving with a sieve (C) having meshes smaller than the meshes of the sieve (B) makes it possible to remove excess colloidal particles to concentrate the biological particles as a target and to perform the imaging efficiently. In addition, using a sieve having meshes smaller than the meshes of the sieve (B) makes it possible to reduce the loss of biological particles as a detection target. The meshes of the sieve (C) are not particularly limited as long as the meshes are smaller than the meshes of the sieve (B) used in step (1) and examples thereof include 30 to 63 μm.

In this step, while allowing the fluid 4 including at least a part of the supernatant fraction (S0) and the supernatant fractions (S1) to (Sn) prepared as described above to flow in the flow cell 31, the fluid 4 flowing in the flow cell 31 is imaged. It is possible for the flow cell 31 to be the same as in the method of the first embodiment. In addition, it is also possible for the method of introducing the fluid 4 into the flow cell 31, the method of imaging the fluid 4 flowing in the flow cell 31, and the like, to be performed with the same methods as the methods of the first embodiment.

It is possible to use images of biological particles acquired by the method of the present embodiment for analysis for classifying organism species in the same manner as the image acquired by the method of the first embodiment.

According to the method of the present embodiment, since it is possible to remove sediment by a sieving treatment and a centrifugation treatment, it is possible to efficiently acquire images of biological particles even for samples including sediment. In addition, in step (II'), since the colloidal solution is added to the precipitate obtained by centrifugation and further centrifugation is carried out, it is possible to recover the biological particles even in a case where the biological particles remain in the precipitate.

(Optional Step)

In the same manner as the method of the first embodiment, the method of the present embodiment may further include a step of recovering the fluid 4 for which the imaging is finished in addition to steps (I), (II), (II'), and (III') described above. Recovering the fluid 4 for which the imaging is finished makes further analysis of the biological particles included in the fluid 4 possible. The method of recovering the fluid 4 for which the imaging is finished may also be performed in the same manner as in the method of the first embodiment.

<Apparatus for Pretreating Sample Including Biological Particles>

In one embodiment, the present invention provides an apparatus for pretreating a sample including biological particles for realizing the method of pretreating a sample including biological particles described above. An apparatus for pretreating a sample including biological particles according to the present embodiment is provided with a sieving section which is provided with a sieve (A) having meshes of 250 to 1000 μm and a sieve (B) having meshes of 32 to 63 μm, and which performs sieving of a sample including biological particles as a detection target to acquire a fraction (1b) which passes through the sieve (A) and does not pass through the sieve (B); a colloidal solution addition section for adding a colloidal solution to the fraction (1b) acquired by the sieving section; a centrifugation section for subjecting the fraction (1b) to which the colloidal solution was added to centrifugation; and a supernatant fraction-acquiring section for acquiring a supernatant fraction after the centrifugation in the centrifugation section.

A description will be given below of an example of a configuration of an apparatus for pretreating a sample including biological particles according to the present embodiment.

Figure 3:
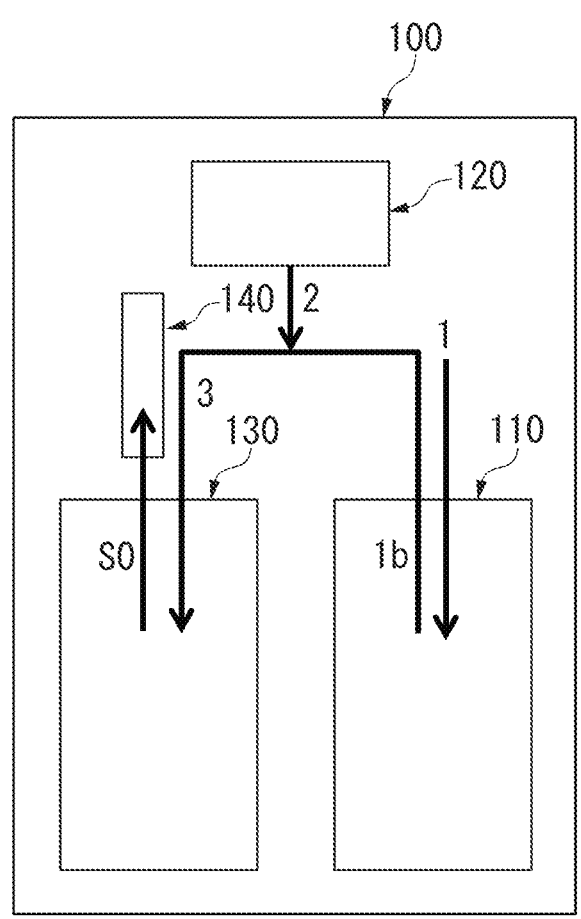
FIG. 3 shows a configuration example of an apparatus for pretreating a sample including biological particles according to one embodiment of the present invention.

FIG. 3 shows an example of a configuration of an apparatus for pretreating a sample including biological particles of the present embodiment. A pretreatment apparatus 100 shown in FIG. 3 is provided with a sieving section 110, a colloidal solution addition section 120, a centrifugation section 130, and a supernatant fraction-acquiring section 140.

The sieving section 110 is a unit for sieving the sample 1 including biological particles as a detection target and acquiring a fraction (1b) which passes through a sieve (A) having meshes of 250 to 1000 μm and does not pass through a sieve (B) having meshes of 32 to 63 μm. The sieving section 110 is provided with at least a sieve (A) having meshes of 250 to 1000 μm and a sieve (B) having meshes of 32 to 63 μm, and the sample 1 is sieved by these sieves. The sieving section 110 may be configured as shown in FIG. 1a, for example. In the example of FIG. 1a, there is a configuration in which a sieve (A) having meshes of 250 to 1000 μm and a sieve (B) having meshes of 32 to 63 μm are installed in the container 10, and sieving is performed while carrying out shaking with the shaker 13. After finishing the sieving, a fraction (1b) which passes through the sieve (A) having meshes of 250 to 1000 µm and does not pass through the sieve (B) having meshes of 32 to 63 µm is acquired.

Here, the configuration of the sieving section 110 is not limited to the example in FIG. 1a, and for example, the sieve (A) and the sieve (B) may be installed in separate containers. In such a case, after finishing the sieving, it is possible to separate the containers in which each sieve is installed and to acquire fractions (1b) for each container in which the sieve (B) is installed.

The colloidal solution addition section 120 is a unit for adding the colloidal solution 2 to the fraction (1b) acquired by the sieving section 110. The colloidal solution 2 is the same as used in step (II) in "<Method of Acquiring Image of Biological Particles>" described above. It is possible to configure the colloidal solution addition section 120, for example, to add the colloidal solution 2 to the fraction (1b) with a pipette, a tube, a glass tube, or the like.

The centrifugation section 130 is a unit for performing centrifugation on the fraction (1b) to which the colloidal solution 2 was added in the colloidal solution addition section 120. In FIG. 3, a mixture of the fraction (1b) and the colloidal solution 2 is shown as the mixture 3. It is possible for the centrifugation section 130 to be provided with a typical centrifuge. The conditions for centrifugation in the centrifugation section 130 may be set by an operation panel or the like.

The supernatant fraction-acquiring section 140 is a unit for acquiring a supernatant fraction (S0) after the centrifugation in the centrifugation section 130. The supernatant fraction-acquiring section 140 may acquire the supernatant fraction (S0) with, for example, a pipette, a tube, a glass tube, or the like, or may be configured to move the supernatant fraction (S0) directly from a centrifuge tube to another container.

A description will be given of an example of the operation of the pretreatment apparatus 100 provided with the above configuration.

First, the sample 1 including biological particles as a detection target is put into the sieving section 110. In the sieving section 110, the sample 1 is sieved, and a fraction (1b) which passes through a sieve having meshes of 250 to 1000 µm and does not pass through a sieve having meshes of 32 to 63 µm is acquired. Many of the sediment particles included in the sample 1 are removed by sieving with the sieving section 110.

The colloidal solution 2 is added by the colloidal solution addition section 120 to the fraction (1b) acquired by the sieving section 110. Due to this, the mixture 3 of the fraction (1b) and the colloidal solution 2 is prepared.

The mixture 3 is introduced into the centrifugation section 130 and subjected to centrifugation. Due to this, the mixture 3 is separated into a supernatant fraction (S0) and a precipitate (P0). The supernatant fraction (S0) includes the biological particles as a detection target and the precipitate (P0) includes sediment particles. It is possible to acquire a supernatant fraction (S0) including almost no sediment particles by centrifugation in the centrifugation section 130. Thereafter, the supernatant fraction (S0) is acquired by the supernatant fraction-acquiring section 140 and is appropriately prepared to complete the pretreatment of the sample including the biological particles.

Since the pretreatment apparatus for a sample including biological particles of the present embodiment is provided with the above-described configuration, it is possible to prepare a sample having sufficient quality for subsequent analysis even for a sample including a lot of sediment particles. In addition, the sample prepared by the pretreatment apparatus for a sample including biological particles according to the present embodiment makes it possible to acquire an image having sufficient image quality for subsequent analysis in a case where an image of biological particles is acquired by an image-acquiring apparatus or the like.

Here, the pretreatment apparatus 100 may be provided with other configurations than the configurations described above. For example, the pretreatment apparatus 100 may be provided with a precipitation suspension section. The precipitation suspension section is a unit for suspending the precipitate after the centrifugation in the centrifugation section 130 and adding the colloidal solution 2 to the precipitate (P0) after the supernatant fraction (S0) is acquired by the supernatant fraction-acquiring section 140. The precipitate (P0) suspended in the colloidal solution 2 in the precipitation suspension section is again subjected to centrifugation in the centrifugation section 130. After centrifugation, the supernatant fraction (S1) is acquired by the supernatant fraction-acquiring section 140. Due to this, it is possible to recover the biological particles even in a case where biological particles as a detection target remain in the precipitate (P0). In addition, the precipitate (P1) obtained by centrifugation again may be further suspended in the colloidal solution 2 in the precipitation suspension section, and centrifugation may be performed again in the centrifugation section 130. In this manner, when the supernatant fraction obtained by the $n^{th}$ centrifugation is the supernatant fraction (Sn) and the precipitate obtained by the $n^{th}$ centrifugation is precipitate (Pn), the colloidal solution 2 may be added to the precipitate (Pn−1) to cause suspension, and subjected to centrifugation n times. The number of times to suspend the precipitates (P0) to (Pn−1) in the precipitation suspension section may be set by an operation panel or the like.

The precipitation suspension section may be configured to suspend the precipitate by adding the colloidal solution 2 to a centrifuge tube with a pipette, a tube, a glass tube, or the like after acquiring the supernatant fraction and shaking the centrifuge tube, or may be configured to suspend the precipitate by performing pipetting or the like after the addition of the colloidal solution 2. In addition, it is also possible for the colloidal solution addition section 120 to perform the addition of the colloidal solution 2.

In addition, the pretreatment apparatus 100 may be provided with a supernatant fraction preparation section. The supernatant fraction preparation section is a unit for further preparing the supernatant fractions (S0) to (Sn) acquired by the supernatant fraction-acquiring section 140 for subsequent analysis. For example, it is possible for the supernatant fraction preparation section to be configured to mix the supernatant fractions (S0) to (Sn) acquired by the supernatant fraction-acquiring section 140. In addition, a configuration may be provided in which a colloidal solution is added to the supernatant fractions (S0) to (Sn). Alternatively, a configuration may be provided in which a sieve (C) having meshes smaller than the meshes of the sieve (B) is provided, a fraction which does not pass through the sieve (C) is acquired by sieving the supernatant fractions (S0) to (Sn), and a colloidal solution is added to the fraction.

It is possible for the pretreatment apparatus 100 to be further provided with a control section or the like for controlling the operation of the entire apparatus.

<Biological Particle Image-Acquiring Apparatus>

In one embodiment, the present invention provides a biological particle image-acquiring apparatus for realizing the method of acquiring an image of biological particles described above. The biological particle image-acquiring apparatus of the present embodiment is provided with a sieving section which is provided with a sieve (A) and a sieve (B) having meshes smaller than meshes of the sieve (A), and which performs sieving of a sample including biological particles as a detection target to acquire a fraction (1b) which passes through the sieve (A) and does not pass through the sieve (B); a colloidal solution addition section for adding a colloidal solution to the fraction (1b) acquired by the sieving section; a centrifugation section for subjecting the fraction (1b) to which the colloidal solution was added to centrifugation; a supernatant fraction-acquiring section for acquiring a supernatant fraction after the centrifugation in the centrifugation section; and an imaging section which is provided with a flow cell and a camera and which allows a fluid including at least a part of the supernatant fraction acquired by the supernatant fraction-acquiring section to flow in the flow cell and images the fluid flowing in the flow cell with the camera. The sieve (A) has meshes smaller than whichever is larger of either of an inner diameter of the flow cell in a width direction and a depth direction.

A description will be given below of an example of the configuration of the biological particle image-acquiring apparatus of the present embodiment.

Figure 4:
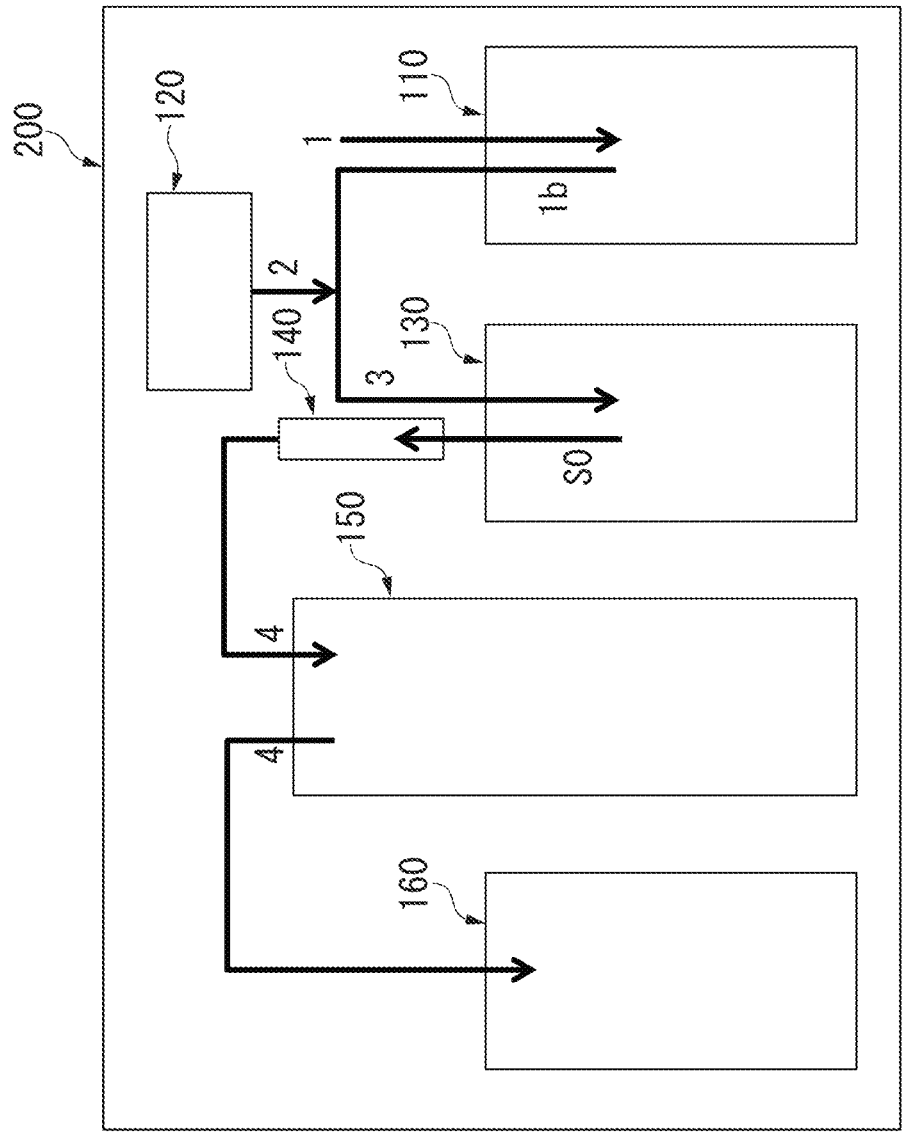
FIG. 4 shows a configuration example of a biological particle image-acquiring apparatus according to one embodiment of the present invention.
Figure 5:
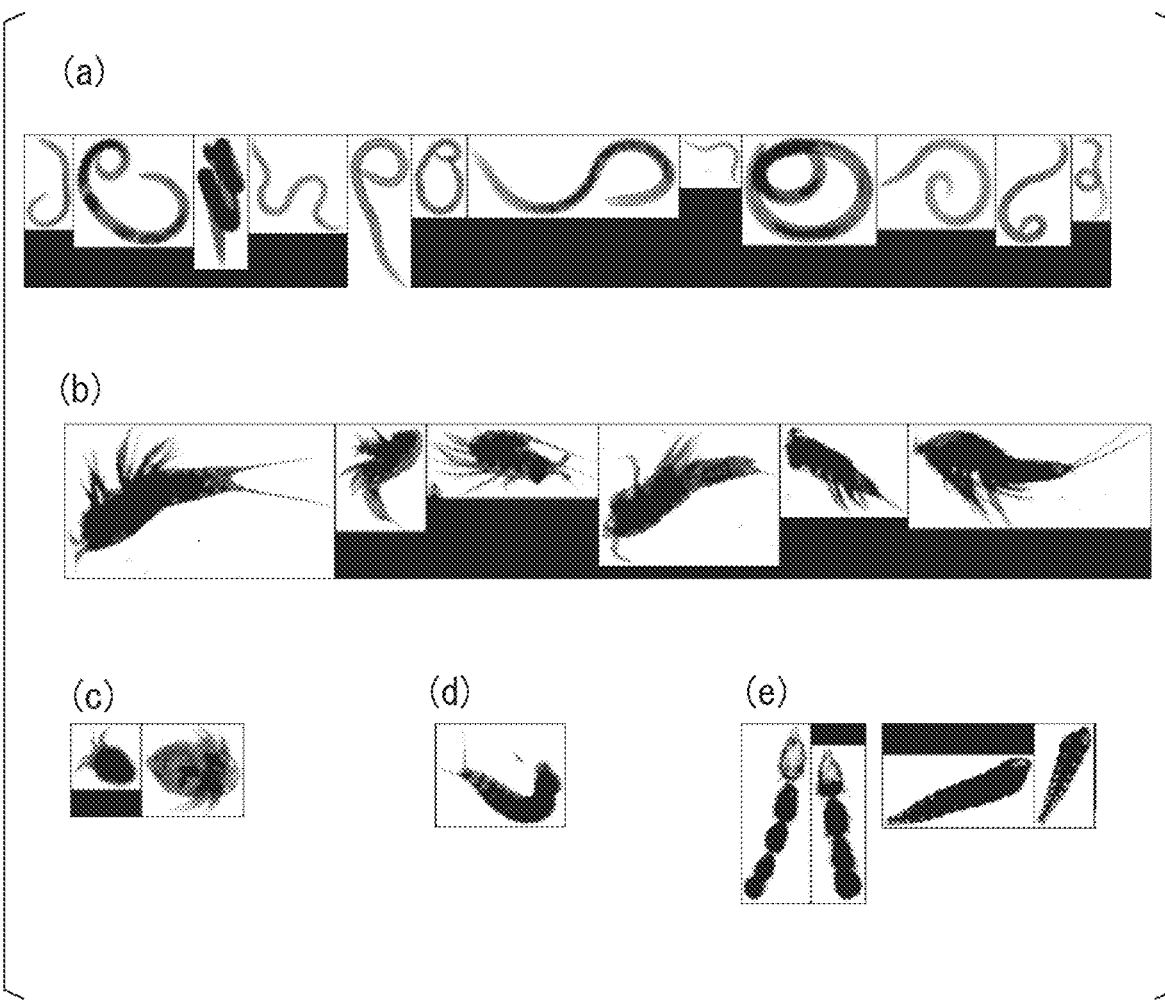
FIG. 5 shows examples of images of meiofauna acquired by a method according to one embodiment of the present invention. (a) shows nematodes, (b) shows copepods, (c) shows nauplius larvae, (d) shows kinorhyncha, and (e) shows foraminifera.

FIG. 4 shows an example of the configuration of the biological particle image-acquiring apparatus of the present embodiment. The biological particle image-acquiring apparatus 200 shown in FIG. 4 is provided with the sieving section 110, a colloidal solution addition section 120, the centrifugation section 130, a supernatant fraction-acquiring section 140, an imaging section 150, and a fluid recovery section 160.

The sieving section 110 is a unit for sieving the sample 1 including the biological particles as a detection target and acquiring a fraction (1b) which passes through the sieve (A) and does not pass through the sieve (B). The sieve (A) has larger meshes than the sieve (B). The sieve (A) is for removing particles larger than the biological particles as a detection target. It is possible to appropriately select the meshes of the sieve (A) based on the size of the biological particles as a detection target. However, the meshes of the sieve (A) are set to be the maximum value or less of the size able to pass through the flow cell of the imaging section 150. Specifically, the sieve (A) has meshes smaller than whichever is larger of either of the inner diameter in the width direction and in the depth direction of the flow cell. Alternatively, the meshes of the sieve (A) may be meshes smaller than the maximum size through which biological particles are able to pass in the flow path design of the flow cell.

The sieve (B) has smaller meshes than the sieve (A). The sieve (B) is for removing particles smaller than the biological particles as a detection target. It is possible to appropriately select the meshes of the sieve (B) based on the size of the biological particles as a detection target. However, the sieve (B) preferably has meshes which are the minimum value or less of the particle diameter on which the camera of the imaging section 150 is able to focus. The minimum value of the particle diameter on which the camera of the imaging section 150 is able to focus is defined by the inner diameter in the depth direction of the flow cell provided in the imaging section 150 and the depth of focus of the camera. Accordingly, the meshes of the sieve (B) may be selected based on the size of the biological particles as a detection target, the inner diameter in the depth direction of the flow cell, and the depth of focus of the camera.

For example, it is possible to generally express the depth of focus of a camera by Berek's formula, as shown in Equation (1).

(Equation 1)

$$D.O.F = \frac{\omega \times 250{,}000}{NA \times M} + \frac{\lambda}{2(NA)^2} \ (\mu m) \tag{1}$$

D.O.F: Depth of Focus
ω: Resolving power of eyes (0.014: in a case where optical angle of the eye is set to 5 parts)
M: Total magnification
λ: Wavelength of light (λ=0.55 μm in the case of visible light)
NA: Numerical aperture defined by camera Here, for example, when M=1000 and NA=0.90, D.O.F.=0.73 μm. Also, for example, when M=4 and NA=0.90, D.O.F.=182.5 μm.

In addition, in a case of a ½-inch HD camera, the CCD size is 6.4 mm (W)×4.8 mm (H), the CCD pixel number is 1980 (W)×1080 (H), and the resolution has a width (W) of 3.2 μm and a height (H) of 4.4 μm. Accordingly, when M=4, the minimum value of the particle diameter on which the camera is able to focus is 0.8 μm in width (W) and 1.1 μm in height (H).

When the depth of focus and the camera specification are set in this manner, the total magnification (M) is determined, and the minimum value of the particle diameter on which the camera is able to focus is determined.

Since the limit resolution in the optical system is 0.2 μm, the meshes of the sieve (B) may be 0.2 μm or more. For example, the meshes of the sieve (B) may be 1 μm or more, 10 μm or more, or 20 μm or more in accordance with the details of the biological particles as a detection target.

In a case where the biological particles as a detection target are meiofauna, examples thereof include 250 to 1000 μm as meshes of the sieve (A) and 32 to 62 μm as meshes of the sieve (B).

Based on the size of the biological particles as a detection target, the size of the flow cell, and the depth of focus of the camera, the operator selects appropriate meshes for each of the sieve (A) and the sieve (B), which may be installed in the sieving section 110. Alternatively, the sieving section 110 may be provided with a plurality of types of sieves having different meshes, and the sieve (A) and the sieve (B) may be selected according to the size of the biological particles as a detection target and the flow cell, and the depth of focus of the camera. In such a case, depending on the selection by the operator, the sieve (A) and the sieve (B) may be installed in the sieving section 110. Alternatively, the biological particle image-acquiring apparatus 200 may automatically select the sieve (A) and the sieve (B) according to the size of the biological particles as a detection target and the flow cell, and the depth of focus of the camera, and install the sieve (A) and the sieve (B) in the sieving section 110. The biological particle image-acquiring apparatus 200 may be provided with an input unit or the like for inputting the size of the biological particles as a detection target, the size of the flow cell, the depth of focus of the camera, and the like.

It is possible for other configurations of the sieving section 110 to be the same as described in the pretreatment apparatus 100 for a sample including biological particles.

The colloidal solution addition section 120, the centrifugation section 130, and the supernatant fraction-acquiring section 140 are the same as described in the pretreatment apparatus 100 for a sample including biological particles.

The imaging section 150 is a unit for imaging the fluid flowing in the flow cell with a camera while allowing the fluid 4 including at least a part of the supernatant fraction (S0) acquired by the supernatant fraction-acquiring section 140 to flow in the flow cell. The imaging section 150 includes at least a flow cell and a camera.

For example, the imaging section 150 may have a configuration as shown in FIG. 1d. In the example of FIG. 1d, there is a configuration in which the flow cell 31 and the camera 32 are provided, the objective lens 33 is installed between the flow cell 31 and the camera 32, and the camera 32 images the frame 40 portion of the flow cell 31 via the objective lens 33. In addition, light is irradiated on the frame 40 portion by the light source 34.

The flow cell 31 may be appropriately selected according to the biological particles as the detection target. For example, in a case where the detection target is meiofauna, it is possible to set the inner diameter of the flow cell 31 in the depth direction with respect to the imaging plane to 150 to 500 µm. In addition, a pump or the like may be connected to the downstream side of the flow cell 31, and the fluid introduced into the flow cell 31 may be suctioned by the pump or the like to create a fluid flow in the flow cell 31.

The camera 32 may be for a still image or may be for a moving image. In a case where the camera 32 is for a still image, it is preferable that continuous imaging be possible, and it is more preferable to perform continuous imaging at predetermined time intervals. In addition, the imaging interval may be set by an operation panel or the like.

The objective lens 33 is used to acquire an enlarged image of the frame 40. The magnification of the objective lens 33 may be appropriately selected according to the biological particles as the detection target. For example, in a case where the detection target is meiofauna, it is possible to use an objective lens with a magnification of 10 to 100 times.

The light source 34 is used to irradiate the frame 40 with light to acquire a clearer image. The light source 34 may intermittently irradiate light according to the imaging interval by the camera 32 or may constantly irradiate light, but is preferably a flash light source which irradiates light at predetermined intervals. In addition, the irradiation interval may be set by an operation panel or the like.

Light irradiated from the light source 34 is not particularly limited, but is preferably visible light. In addition, in a case where the biological particles as the detection target are stained with a fluorescent dye, the biological particles may be irradiated with light having a wavelength exciting the fluorescent dye.

A description will be given of an example of the operation of the biological particle image-acquiring apparatus 200 provided with the above configuration.

First, the sample 1 including biological particles as a detection target is put into the sieving section 110. In the sieving section 110, the sample 1 is sieved, and a fraction (1b) which passes through the sieve (A) and does not pass through the sieve (B) is acquired. Many of the sediment particles included in the sample 1 are removed by sieving in the sieving section 110.

The colloidal solution 2 is added to the fraction (1b) acquired by the sieving section 110 by the colloidal solution addition section 120. Due to this, the mixture 3 of the fraction (1b) and the colloidal solution 2 is prepared.

The mixture 3 is introduced into the centrifugation section 130 and subjected to centrifugation. Due to this, the mixture 3 is separated into a supernatant fraction (S0) and a precipitate (P0). The supernatant fraction (S0) includes the biological particles as the detection target and the precipitate (P0) includes sediment particles. It is possible to acquire a supernatant fraction (S0) including almost no sediment particles by centrifugation in the centrifugation section 130. Thereafter, the supernatant fraction (S0) is acquired by the supernatant fraction-acquiring section 140 and appropriately prepared as the fluid 4 including at least a part of the supernatant fraction (S0).

The fluid 4 is introduced into the imaging section 150 and imaged. In the imaging section 150, the fluid 4 flows in the flow cell and an image of the fluid present in the imaging frame on the flow cell is imaged by the camera. In this manner, it is possible for the biological particle image-acquiring apparatus 200 to acquire images of biological particles as the detection target.

Since the biological particle image-acquiring apparatus of the present embodiment has the configuration described above, it is possible to acquire an image having sufficient image quality for subsequent analysis even with a sample including a lot of sediment particles. In addition, since it is possible to automatically perform the operations up to image acquisition, it is possible to eliminate the time and effort required in the related art for analysis by a microscope.

The biological particle image-acquiring apparatus 200 may be provided with other configurations than the above configuration. In the example shown in FIG. 4, the biological particle image-acquiring apparatus 200 is provided with the fluid recovery section 160.

The fluid recovery section 160 is a unit for recovering the fluid 4 for which the imaging in the imaging section 150 is finished. For example, it is possible for the fluid recovery section 160 to have a configuration provided with a container for recovering the fluid 4, a tube for guiding the fluid 4 to the container, a pump for making a flow of the fluid 4 in the tube, and the like. For example, it is possible to have a configuration in which a tube is connected to the downstream end of the flow cell 31 in the imaging section 150, and the tube is connected to a container in the fluid recovery section 160.

In addition, a configuration may be adopted in which a pump is connected to the container, the air in the container is discharged, and the fluid 4 which has passed through the flow cell is recovered in the container via the tube.

It is possible to use the fluid 4 recovered by the fluid recovery section 160 for further analysis.

In addition, the biological particle image-acquiring apparatus 200 may be provided with a precipitation suspension section, a supernatant fraction preparation sections, and the like in the same manner as the pretreatment apparatus 100 for a sample including biological particles. The precipitation suspension section and the supernatant fraction preparation section are the same as described in the pretreatment apparatus 100.

It is possible for the biological particle image-acquiring apparatus 200 to further include an image display section which displays the image acquired by the imaging section 150, an image analysis section which analyzes the acquired image, a control section which controls the operation of the entire device, and the like.

EXAMPLES

A description will be given below of the present invention with reference to Examples, but the present invention is not limited to the following Examples.

Test Example 1

[Samples for Analysis]

Sediment samples obtained at three points (water depth 560 m, 3300 m, and 7100 m) off Kushiro, Hokkaido, were used.

[Sieving of Samples]

The sediment samples were sieved using six sieves with meshes of 1 mm, 500 μm, 250 μm, 125 μm, 63 μm, and 38 μm. The number of meiofauna captured by each of the sieves was confirmed by a microscope.

[Results]

Table 1 shows the number of meiofauna captured by each sieve. Approximately 80% of the individuals were in the sieving section of 63 to 250 μm.

TABLE 1

| Sieve meshes | Water depth: 560 m | | Water depth: 3300 m | | Water depth: 7100 m | |
| --- | --- | --- | --- | --- | --- | --- |
| | Population density (ind./10 cm$^2$) | Ratio (%) | Population density (ind./10 cm$^2$) | Ratio (%) | Population density (ind./10 cm$^2$) | Ratio (%) |
| >1 mm | 1.12 | 0.36 | 0.74 | 0.19 | 0.74 | 0.34 |
| >500 μm | 5.95 | 1.90 | 2.97 | 0.78 | 2.97 | 1.37 |
| >250 μm | 44.97 | 14.40 | 16.35 | 4.27 | 11.89 | 5.50 |
| >125 μm | 123.40 | 39.52 | 169.49 | 44.27 | 99.61 | 46.05 |
| >63 μm | 110.02 | 35.24 | 145.70 | 38.06 | 65.42 | 30.24 |
| >38 μm | 26.76 | 8.57 | 47.58 | 12.43 | 35.68 | 16.49 |

Test Example 2

[Samples for Analysis]

Sediment samples obtained at 4 points (water depth 72 in, 303 in, 1064 in, 1677 m) off Otsuchi Bay, Iwate prefecture, were used.

[Sample Pretreatment for Acquiring Analysis Image]

The sediment samples were fixed with 5% neutralized formalin and the organisms in the sediment samples were stained with Rose Bengal (final concentration 0.05 g/L).

Approximately 26.4 mL of the sediment samples after the dyeing operation was sieved while shaking. For sieving, a sieve having meshes of 250 μm and a sieve having meshes of 63 μm were used and samples which had passed through a sieve having meshes of 250 μm and did not pass through a sieve having meshes of 63 μm were recovered.

The recovered sample was placed in a 50-mL centrifuge tube and approximately 30 mL of colloidal silica (LUDOX HS-40, SIGMA-ALDRICH) was added thereto to suspend the sample in the colloidal silica. Thereafter, the sample was centrifuged at 800 G for 10 minutes using a centrifugal separator (LC 200, TOMY). The supernatant was collected from the centrifuge tube after centrifugation and collected on a sieve having meshes of 32 μm.

After collecting the supernatant, approximately 30 mL of colloidal silica was added to the precipitate in the centrifuge tube, and the precipitate was suspended in the colloidal silica. Thereafter, the sample was centrifuged at 800 G for 10 minutes using a centrifugal separator. The supernatant was collected from the centrifuge tube after centrifugation and collected on a sieve having meshes of 32 μm. The operation was performed one more time.

A sample collected on a sieve having meshes of 32 μm from the above-described supernatant after three centrifugations was suspended in approximately 10 mL of colloidal silica and recovered in a new 50-mL centrifuge tube.

[Acquisition of Analysis Images]

The acquisition of analysis images was performed using FlowCAM (Fluid Imaging Technologies), a counting device of flowing particle with a camera. An objective lens having a magnification of four times was used, and a flow cell having an inner diameter of 300 μm in the depth direction with respect to the imaging plane of the camera was used.

In addition, in order to recover the sample passed through FlowCAM, a new 50-mL centrifuge tube was prepared. The upper portion of the centrifuge tube was hermetically sealed with parafilm, two tubes were inserted, and the other end of one tube was connected to the downstream side of the flow cell. The other end of the other tube was connected to a peristatic pump (Fisher Scientific). With this configuration, when the peristatic pump is operated, a sample flows from the flow cell to the tube, and the sample is recovered in the centrifuge tube. In this manner, the sample which had passed through the FlowCAM was collected in a centrifuge tube.

The flow cell and the tube connected to the flow cell were filled in advance with a colloidal silica solution before the introduction of the sample.

In the configuration as described above, the sample recovered in the centrifuge tube was gently stirred, introduced into a FlowCAM flow cell using a Pasteur pipette, and imaged. Imaging was performed in Auto Image Mode, and the Auto Image Rate (the number of images imaged per second) was set to 20. In addition, the Flash Duration was set to 10 μs.

[Image Analysis]

The imaged image was sorted by the sort function Red/Blue Ratio of the software VisualSpreadSheet attached to FlowCAM, each image was confirmed visually, and the organisms were selected and counted for each higher classification group. Here, although the selection was performed visually, biological images may be automatically selected and classified by a program or the like from the form of the organisms obtained from each image and the morphological features such as spines. The selection of biological images may be performed by image analysis software, artificial intelligence (A.I.), or the like.

[Results]

The centrifuge tube used for introducing the sample into FlowCAM and the inside of the tube after finishing counting were examined, and there were a few organisms remaining.

FIGS. 5a to 5e show examples of images imaged by FlowCAM. The images captured with FlowCAM were sufficient quality to select the organisms visually.

Figure 6:
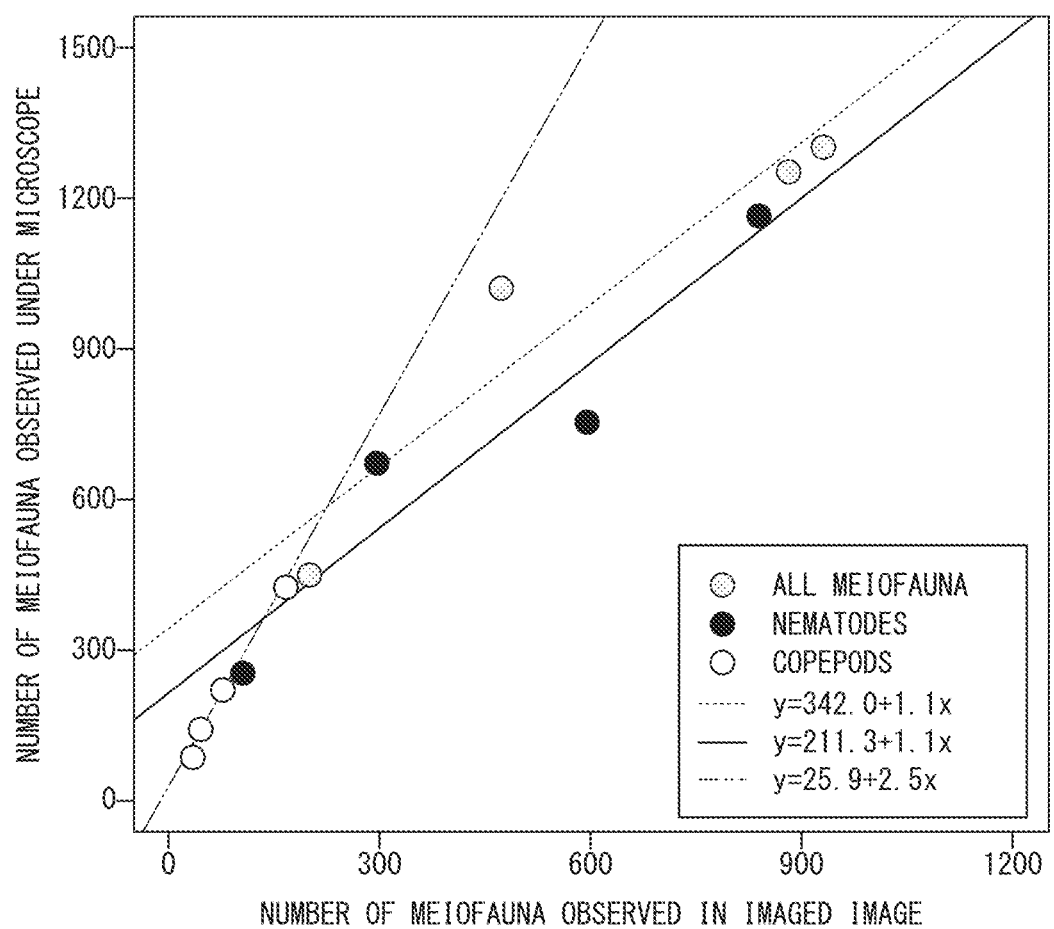
FIG. 6 shows correlations between the number of meiofauna counted based on an image acquired by the method according to one embodiment of the present invention and the number counted under a microscope.

The imaging efficiency was calculated by comparing the number of organisms observed in FlowCAM with the number collected in the centrifuge tube after passing through FlowCAM. As a result, the imaging efficiency was 57.9±14.8% for the meiofauna as a whole, 58.9±19.6% for the nematodes, and 34.6±3.7% for the copepods. In addition, the number counted with FlowCAM and the number counted by the microscope with the sample collected in the centrifuge tube showed a significant correlation (total meiofauna: r=0.95, $p<0.05$; nematodes: r=0.95, $p<0.05$; copepods: r=1.00, $p<0.01$; FIG. 6).

From the above, it is clear that this method is able to obtain analysis results with a high correlation with the analysis results of the number of organisms obtained by the microscopic methods of the related art.

INDUSTRIAL APPLICABILITY

According to the present invention, a technique is provided which is capable of quickly analyzing biological particles even in a case where sediment particles are present.

REFERENCE SIGNS LIST

1 SAMPLE
1a FRACTION WHICH DOES NOT PASS THROUGH A SIEVE HAVING MESHES OF 250 TO 1000 μm
1b FRACTION WHICH PASSES THROUGH A SIEVE HAVING MESHES OF 250 TO 1000 μM AND DOES NOT PASS THROUGH A SIEVE HAVING MESHES OF 32 TO 63 μm
1c FRACTION WHICH PASSES THROUGH A SIEVE HAVING MESHES OF 32 TO 63 μm
2 COLLOIDAL SOLUTION
3 MIXTURE INCLUDING FRACTIONS (1b) AND COLLOIDAL SOLUTION 2
4 FLUID
5a to 5c BIOLOGICAL PARTICLES
6 SUSPENSION
10 CONTAINER
13 SHAKER
20 CENTRIFUGE
21 CENTRIFUGE TUBE
30 IMAGING APPARATUS
31 FLOW CELL
32 CAMERA
33 OBJECTIVE LENS
34 LIGHT SOURCE
40 FRAMES
41 IMAGE
100 APPARATUS FOR PRETREATING SAMPLE INCLUDING BIOLOGICAL PARTICLES
110 SIEVING SECTION
120 COLLOIDAL SOLUTION ADDITION SECTION
130 CENTRIFUGATION SECTION
140 SUPERNATANT FRACTION-ACQUIRING SECTION
150 IMAGING SECTION
160 FLUID RECOVERY SECTION
200 BIOLOGICAL PARTICLE IMAGE-ACQUIRING APPARATUS
A SIEVE HAVING MESHES OF 250 TO 1000 μm
B SIEVE HAVING MESHES OF 32 TO 63 μm
S0 to Sn SUPERNATANT FRACTION
P0 to Pn PRECIPITATION

The invention claimed is:

1. A method of acquiring an image of biological particles, the method comprising:
a step of acquiring a fraction (1b) of a sample including biological particles as a detection target, the fraction (1b) is a fraction which passes through a sieve (A) having meshes of 250 to 1000 μm and does not pass through a sieve (B) having meshes of 32 to 63 μm;
a step of adding a colloidal solution having a density of 1.10 to 2.45 g/cm$^3$ to the fraction (1b) to obtain a resultant solution, subjecting the resultant solution to centrifugation, and acquiring a supernatant fraction (S0) after the centrifugation;
a step of preparing the supernatant fraction (S0) by sieving the supernatant fraction (S0) with a sieve (C) having meshes smaller than meshes of the sieve (B) to acquire a fraction which does not pass through the sieve (C), and adding the colloidal solution to the fraction; and
a step of allowing a fluid including at least a part of the prepared supernatant fraction (S0) to flow in a flow cell and imaging the fluid flowing in the flow cell, wherein the fluid includes the colloidal solution.

2. The method of acquiring an image of biological particles according to claim 1, further comprising:
a step of performing suspending a precipitate (Pn−1) after centrifugation in the colloidal solution to obtain a colloidal solution including the precipitate (Pn−1), performing centrifugation of the colloidal solution including the precipitate (Pn−1), and acquiring a supernatant fraction (Sn) after the centrifugation, n times, wherein n is an integer of 1 or more, the precipitate (Pn−1) is a precipitate obtained after the (n−1)$^{th}$ centrifugation, and the supernatant fraction (Sn) is the supernatant fraction obtained after the n$^{th}$ centrifugation;
a step of preparing the supernatant fractions (S1) to (Sn) by sieving the supernatant fractions (S1) to (Sn) with a sieve (C) having meshes smaller than meshes of the sieve (B) to acquire a fraction which does not pass through the sieve (C), and adding the colloidal solution to the fraction; and
a step of allowing a fluid including at least a part of the prepared supernatant fractions (S1) to (Sn) of the n times to flow in a flow cell and imaging the fluid flowing in the flow cell, wherein the fluid includes the colloidal solution.

3. The method of acquiring an image of biological particles according to claim 2,
wherein a part or all of the supernatant fraction (S0) and the supernatant fractions (S1) to (Sn) are mixed and the mixture is sieved with the sieve (C).

4. The method of acquiring an image of biological particles according to claim 1, further comprising:
a step of recovering the fluid for which the imaging is finished.

5. The method of acquiring an image of biological particles according to claim 1,
wherein the colloidal solution is colloidal silica.

6. The method of acquiring an image of biological particles according to claim 1,
wherein the biological particles have been stained with a dye.

7. A biological particle image-acquiring apparatus, comprising:
a sieving section which is provided with a sieve (A) and a sieve (B) having meshes smaller than meshes of the sieve (A), and which performs sieving of a sample including biological particles as a detection target to acquire a fraction (1b) which passes through the sieve (A) and does not pass through the sieve (B);
a colloidal solution addition section for adding a colloidal solution to the fraction (1b) acquired by the sieving section;
a centrifugation section for subjecting the fraction (1b) to which the colloidal solution was added to centrifugation;
a supernatant fraction-acquiring section for acquiring a supernatant fraction after the centrifugation in the centrifugation section;
a supernatant fraction preparation section which is provided with a sieve (C) having meshes smaller than the meshes of the sieve (B), and which acquires a fraction which does not pass through the sieve (C) by sieving the supernatant fraction, and adding a colloidal solution to the fraction; and an imaging section which is provided with a flow cell and a camera and which allows a fluid including at least a part of the supernatant fraction acquired by the supernatant fraction-preparation section to flow in the flow cell and images the fluid flowing in the flow cell with the camera, wherein the fluid includes the colloidal solution, wherein the sieve (A) has meshes smaller than whichever is larger of either of an inner diameter of the flow cell in a width direction and a depth direction, and the sieve (B) has meshes which are a minimum value or more of a particle diameter upon which the camera is able to focus which is defined by an inner diameter of the flow cell in a depth direction and a depth of focus of the camera.

8. The biological particle image-acquiring apparatus according to claim 7, wherein the sieve (A) has meshes of 250 to 1000 μm and the sieve (B) has meshes of 32 to 63 μm.

* * * * *